United States Patent [19]

Kitahara et al.

[11] Patent Number: 5,294,233

[45] Date of Patent: Mar. 15, 1994

[54] ADDITIVE FOR ORGANIC MEDIUM OR THERMOPLASTIC POLYMER

[75] Inventors: Shizuo Kitahara, Kawaguchi; Hiroyuki Watanabe, Yokohama; Takuji Kishimoto, Yokohama; Tetuya Toyoshima, Yokohama; Takafumi Kawanaka, Yokohama; Kohkichi Noguchi, Kamakura, all of Japan

[73] Assignee: Nippon Zeon Co., Ltd., Tokyo, Japan

[21] Appl. No.: 738,603

[22] Filed: Jul. 31, 1991

Related U.S. Application Data

[63] Continuation-in-part of Ser. No. 497,302, Mar. 22, 1990, abandoned, and a continuation-in-part of Ser. No. 477,558, Feb. 9, 1990, abandoned.

[30] Foreign Application Priority Data

| Feb. 10, 1989 | [JP] | Japan | 1-32198 |
| Mar. 22, 1989 | [JP] | Japan | 1-69458 |
| Apr. 28, 1989 | [JP] | Japan | 1-109499 |
| Apr. 28, 1989 | [JP] | Japan | 1-109500 |
| Jul. 31, 1989 | [JP] | Japan | 1-199113 |
| Aug. 11, 1989 | [JP] | Japan | 1-206856 |
| Dec. 28, 1989 | [JP] | Japan | 1-342197 |
| Jan. 5, 1990 | [JP] | Japan | 2-101 |
| Jan. 9, 1990 | [JP] | Japan | 2-2311 |
| Feb. 2, 1990 | [JP] | Japan | 1-23775 |

[51] Int. Cl.$^5$ .................................................. C10L 1/22
[52] U.S. Cl. ............................................ 44/334; 44/341; 44/342; 44/346
[58] Field of Search ................... 44/346, 342, 341, 334

[56] References Cited

U.S. PATENT DOCUMENTS

| 2,897,182 | 7/1959 | de Benneville | 252/51.5 R |
| 3,141,745 | 7/1964 | Calvino | 44/346 |
| 3,483,141 | 12/1969 | Litt et al. | 528/402 |
| 3,488,294 | 1/1970 | Annand | 44/342 |
| 3,502,627 | 3/1970 | Dupont | 252/50 |
| 3,516,944 | 6/1970 | Litt et al. | 44/272 |
| 3,531,427 | 9/1970 | Kervenski et al. | 524/104 |
| 3,536,658 | 10/1970 | Wich | 524/104 |
| 3,644,264 | 2/1972 | Hyde | 524/104 |
| 4,169,836 | 10/1979 | Ryer et al. | 548/238 |
| 4,222,882 | 9/1980 | Brulet et al. | 252/51.5 A |
| 4,257,780 | 3/1981 | Sung | 44/341 |
| 4,313,738 | 2/1982 | Parlman et al. | 252/51.5 R |
| 4,338,206 | 7/1982 | Hammond et al. | 252/51.5 A |
| 4,402,844 | 9/1983 | Trepka | 252/51.5 A |
| 4,614,771 | 9/1986 | Wantanabe | 525/332.9 |
| 4,616,069 | 10/1986 | Wantanabe | 525/332.9 |
| 4,677,153 | 6/1987 | Kitahara | 524/552 |
| 4,702,854 | 10/1987 | Snyder, Jr. et al. | 252/75 |
| 4,791,174 | 12/1988 | Bronstert | 525/332.9 |
| 4,877,415 | 10/1989 | Kapuscinski | 44/330 |
| 5,001,196 | 3/1991 | Kawanaka | 525/375 |

FOREIGN PATENT DOCUMENTS

2265771 10/1975 France .
2055804 3/1981 United Kingdom .

*Primary Examiner*—Ellen M. McAvoy
*Attorney, Agent, or Firm*—Sherman and Shalloway

[57] ABSTRACT

An additive for improving the dispersibility of a particulate substance in an organic medium, a thermoplastic polymer, or a thermosetting resin, is at least one compound having a

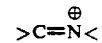

bond in the molecule, including, for example, compounds having an oxazolinium ion in the molecule. The preferred additive compounds are oligomeric or polymeric.

13 Claims, No Drawings

ADDITIVE FOR ORGANIC MEDIUM OR THERMOPLASTIC POLYMER

This application is a continuation-in-part of pending application Ser. No. 07/497,302, filed Mar. 22, 1990, now abandoned, and pending application Ser. No. 07/477,558, filed Feb. 9, 1990 now abandoned.

This invention relates to an additive for improving the dispersibility of a particulate material in an organic medium or a thermoplastic polymer or a thermosetting resin.

Particulate inorganic substances such as titanium dioxide or zinc oxide are incorporated as pigments in various coating compositions such as paints or printing ink, and particular organic substances are also used as a pigment or a film modifying agent. Inorganic substances such as calcium carbonate or silica are used as reinforcing agents or fillers in thermoplastic polymers and rubbers. Furthermore, chops of monofilaments or organic fine particles such as particulate polymers are incorporated as reinforcing agents or surface-treating agents.

Lubricant oils or fuel oils give off a sludge precursor, a sludge binder, a lacquer, a varnish, a resin component or "soot" during use. When these materials flocculate and sediment in the oil, various inconveniences occur. Hence, a detergent-dispersant is used as an essential additive for uniformly and stably dispersing them in the oil without flocculation.

To obtain a dispersion of high performance of a particulate substance in a thermoplastic polymer, it is necessary to disperse fine particles of an inorganic or organic material uniformly in a solid thermoplastic polymer or a solution of the thermoplastic polymer uniformly. Various dispersants or coupling agents have been proposed in order to improve the dispersibility of the inorganic or organic fine particles or to improve adhesion of the fine particles on an interface between the thermoplastic polymer and the inorganic or organic fine particles.

These dispersants or coupling agents include, for example, silane coupling agents, titanium coupling agents, metal salts of fatty acids, zinc salts of high-molecular weight fatty acids, high-molecular-weight aliphatic hydrophilic fatty acid esters and various surface active agents. The use of these compounds improves adhesion on an interface between the polymer and the inorganic material, but is not sufficient for the improvement of dispersibility. Furthermore, the type of the particulate substance that can be applied is limited.

It is an object of this invention to provide a novel additive which can be applied to various inorganic and/or organic particulate materials, and improves the dispersibility of inorganic and/or organic particulate materials in thermoplastic polymers, thermosetting resins or organic media.

As a result of extensive investigations in an attempt to achieve the above object, the present inventors found that compounds in which a specific heterocyclic structure or a specific atomic grouping is introduced into the molecule (into the molecular chains or the ends of the molecular chains) markedly improve the dispersibility of various inorganic and organic fine particulate substances in organic media, thermoplastic polymers, and thermosetting resins.

The present inventors also discovered that because the above compounds suppress an increase in viscosity of a system to which inorganic and/or organic particulate substances are added, and the addition of these compounds improves the processability, transportability or fillability of an organic medium, a thermoplastic polymer or thermosetting resin and a particulate substance surface-treated with the above compounds shows good dispersibility in organic media, thermoplastic polymers or thermosetting resins.

The present invention is based on these findings.

Thus, according to this invention, there is provided an additive for improving the dispersibility of a particulate substance in an organic medium, a thermoplastic polymer or a thermosetting resin, said additive comprising at least one compound selected from the group consisting of compounds having a 1,3-oxazine in the molecule, and compounds having a

bond in the molecule, inclusive of compounds having an oxazolinium ion in the molecule.

The additive of this invention is a compound which contains at least one compound selected from the group consisting of compounds having a 1,3-oxazine structure in the molecule, compounds having a

in the molecule, the latter including compounds having an oxazolinium ion in the molecule. Specific examples of these compounds are compounds of general formulae (I) to (IIIc) and general formulae (1a) to (7).

The compounds having a 1,3-oxazine structure in the molecule may be heterocyclic compounds having O and N at the 1- and 3-positions in a 6-membered ring, and may include not only compounds having an oxazine ring typically represented by formula (IIIa), but also having a hetero ring in which the double bonds in the 6-membered ring is partly or wholly saturated or the positions of the double bonds are different such as a 4H, 5H-1,3-oxazine ring of, for example, formula (IIc).

Specific examples of the compounds having a

bond in the molecule are (1) compounds having a 1,3-oxazine structure in which N in the heterocycle is in the form of a quaternary ammonium salt [formulae (Ia) and (Ib)]; (2) compounds having a 1,3-thiazine ring or a 5H,6H-1,3-thiazine ring in which N in the thiazine ring is in the form of a quaternary ammonium salt [formulae (2a) and (2b)]; (3) compounds having an isoxazole ring or an isothiazole ring or a 4H,5H-isoxazole ring (or isothiazole ring) in which N in the isoxazole ring (or isothiazole ring) is in the form of a quaternary ammonium salt [formulae (3a) and (3b)]; (5) compounds having a 1,2-diazole ring or a 4H,5H-1,2-diazole ring, in which N in the diazole ring is in the form of a quaternary ammonium salt [formulae (4a) and (4b)]; (6) compounds having a 2H-pyrrole ring or a 2H,3H,4H-pyrrole ring, in which N in the pyrrole ring is in the form of a quaternary ammonium salt [formulae (5a) and (5b)]; and (7) compounds having an oxazolinium ion in the molecule. Other examples include reaction products obtained by the reaction of polymers (or oligomers)

having bonded thereto alkali and/or alkaline earth metals, with reactants which on reaction with the above polymers produce a $$>C=\overset{\oplus}{N}<$$

bond, for example, 4,4'-bis(diethylamino)benzophenone [for example, formula (6)]. Examples of the compounds having an oxazolinium ion in the molecule are polymers [for example, formula (7)] obtained by cationically polymerizing a 2-oxazoline, and coagulating the resulting polymer with a solvent having no nucleophilic reactivity.

These compounds may include, for example, compounds obtained by introducing atomic groupings of the following general formula in the molecule (into the molecular chains or into the ends of the molecular chains) by using compounds having a carbon-carbon unsaturated bond in the molecular chains (main chains or side chains), for example, polymers having an unsaturated bond in the molecular chains such as alpha-olefins having a long-chain alkyl group, low molecular weight polyethylene, oligomers of alpha-olefins or poly(styrene methacrylate), or polymers to which alkali and/or alkaline earth metal salts bonded thereto by the chemical reactions to be described below, or by cationic polymerization of 2-oxazolines.

[Compounds having a 1,3-oxazine structure]

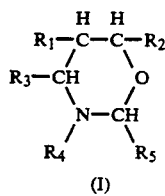
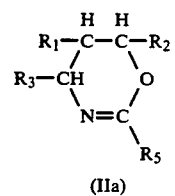

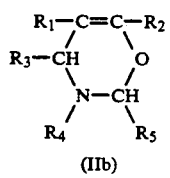
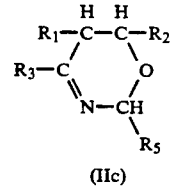

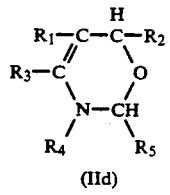
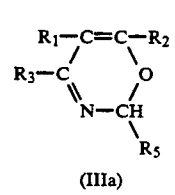

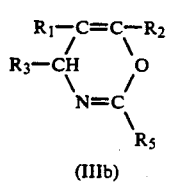
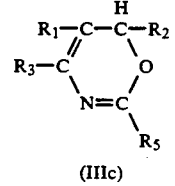

[Compounds having a $>C=\overset{\oplus}{N}<$ bond]

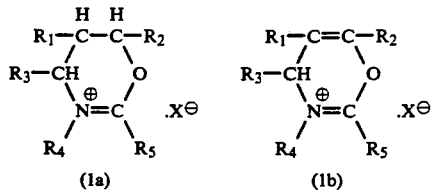

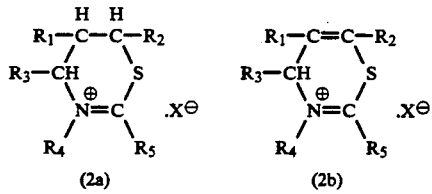

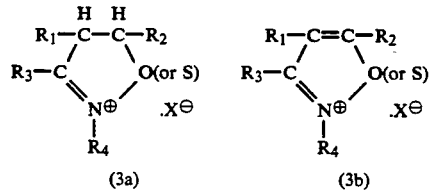

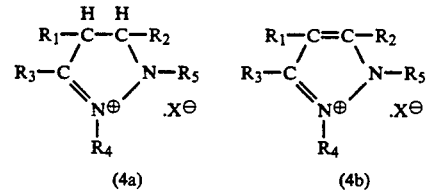

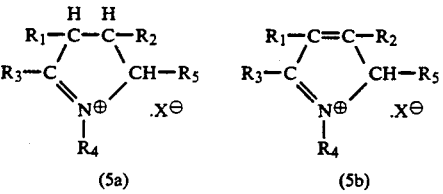

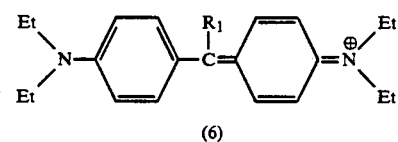

(6)

[Compounds having an oxazolinium ion]

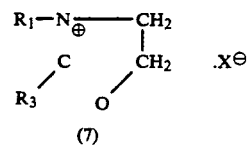

(7)

In the above formulae, $R_1$ represents a part of the backbone chain of each oligomeric or polymeric compound; $R_2$ represents a part of the backbone chain of each oligomeric or polymeric compound, a hydrogen atom or a hydrocarbon group having not more than 6 carbon atoms; $R_3$ to $R_5$ may be identical or different and each represents a hydrocarbon group at least part of which is substituted by a substituent such as a halogen atom, a nitro group, an epoxy group, a carboxyl group or a hydroxyether group; and $X^{\ominus}$ represents an anion.

Some of the methods of producing the additive of this invention are shown below.

(I) The compounds containing a heterocycle having a 1,3-oxazine structure or a

bond may be produced by starting from compounds having a carbon-carbon unsaturated bond such as a carbon-carbon double bond or a triple bond in the molecular chains (at the ends or in the molecular chains).

Examples of the starting compounds having an unsaturated bond at the ends of the molecular chain include alpha-olefins having a long-chain alkyl group such as 1-decene, 1-dodecene, 1-tetradecene, 1-hexadecene, 1-eicosene and 1-tridecene; low molecular weight polymers and oligomers such as low molecular weight polyethylene, liquid or low molecular weight polypropylene and oligomers of alpha-olefins; and macromers such as polybutene, polyisobutylene, polyethylene glycol dimethacrylate, polyethylene glycol diallylate, polypropylene glycol dimethacrylate, polystyrene methacrylate and polystyrene allylate. Examples of the starting compound having an unsaturated bond in the molecular chain are organic compounds having a —C=C— bond, such as 1,9-decadiene, 2,3-dimethylbutene, 2,5-hexadiene, 7-tetradecene and 2,4,4-trimethyl-2-pentene; homopolymers or copolymers such as butadiene, isoprene, piperylene, dicyclopentadiene and ethylidenenorbornene; and copolymers of conjugated dienes and vinyl monomers. Specific examples of these compounds are polybutadiene, polyisoprene, a styrene-butadiene random copolymer, styrene-butadiene block copolymers (A-B type, A-B-A type; A represents a polystyrene block, and B represents a polybutadiene block), a styrene/isoprene random copolymer, styrene/isoprene block copolymers (A-B type and A-B-A type; A represents a polystyrene block and B represents a polyisoprene block), acrylonitrile/butadiene copolymer, butadiene/propylene block copolymer and ethylene/propylene/diene-monomer copolymers, and partially hydrogenated products (with an iodine number of 5 or more) of the above (co)polymers.

Examples of the compounds having a —C≡C— bond include organic compounds, such as 1-decyne, 3,3-dimethyl-1-butyne, heptyne, hexyne, 1,8-nonadiyne and octyne. Compounds which can be used as starting materials in this invention are compounds having a carbon-carbon unsaturated bond in the ends of the molecular chains or in the molecular chains and being soluble, or compatible with organic media or thermoplastic polymers. There is no particular restriction on the molecular weight of these compounds. They may include low molecular weight organic compounds, polymers ranging from oligomers to high molecular weight polymers having a molecular weight of about several hundred thousand. The optimum molecular weight of these polymers may be selected according to the medium used. Typical methods of productions are shown below.

(1) A method comprising reacting a compound having a carbon-carbon unsaturated bond with an organic compound of formula (a)

$$Y_1-CH=N-Y_2 \qquad (a)$$

in which $Y_1$ and $Y_2$ represent an organic atomic grouping, and an organic acid halide in the presence of a Lewis acid.

The organic compound of formula (a) denotes a compound in which specifically $Y_1$ and $Y_2$ represent an aliphatic, alicyclic or aromatic residue which may optionally have an alkoxy, cyano, carboxyl or dialkylamino group. Specific examples of the organic compound (a) include Schiff base compounds such as benzylidene methylamine, benzylidene butylamine, benzylidene aniline, benzylidene cyclohexylamine, propylidene aniline, ethoxybenzylidene butylamine, 4-carbomethoxybenzylidene butylaniline, benzylidene-4-cyanoaniline and dimethylaminobenzylidene butylaniline.

Specific examples of the organic acid halide are acetyl chloride, acetyl bromide, benzoyl chloride, acryloyl chloride, carbomethoxybenzoyl chloride, cinnamoyl chloride and methacryroyl chloride.

Examples of the Lewis acid are $BF_3$, $BF_3O(C_2H_5)_2$, $AlCl_3$, $TiCl_4$, $SnCl_4$, $SbCl_5$, and $AgBF_4$. There is no particular restriction on the reaction conditions. Usually, the reaction is carried out at a temperature of 20° to 80° C. for about 1 to 2 hours in an inert solvent such as benzene, toluene or cyclohexane. Usually, the amounts of the organic compound (a) and the organic acid halide are about 1 to 1.5 moles per mole of the unsaturated compound. The amount of the Lewis acid used is about 0.1 to 1 mole per mole of the organic acid halide. If the unsaturated compound is a polymer, the amounts of the organic compound (a) and the organic acid halide are about 0.1 to 30 parts by weight per 100 parts by weight of the polymer.

This method gives compounds having a heterocyclic structure containing a

bond.

(2) A method which comprises reacting the above compound having a carbon-carbon unsaturated bond in the molecular chain with an N-hydroxymethylamide compound (N-methylol compound) in the presence of a Friedel-Crafts catalyst, and as required, further reacting the product with an alkyl halide, aryl halide, methyl p-toluenesulfonate or dimethyl sulfate.

The N-hydroxymethylamide compound is a reaction product between an amide compound and an aldehyde compound. Examples of the aldehyde compound are aliphatic and aromatic aldehydes such as formaldehyde, butyraldehyde, valeraldehyde and benzaldehyde. Examples of the amide compound are acetamide, benzamide, methoxybenzamide, nitrobenzamide, N-methylbenzamide, butyramide, phthalamide and glutaramide. Copolymers containing an N-methylolacrylamide monomer as one component may also be used as the N-hydroxymethylamide compound.

Examples of the alkyl halide or aryl halide are mainly benzyl bromide, benzyl chloride, bromohexane, bromopropane, 2-chloroethyl ether, chloromethyl ether and chloropentane.

Generally known Friedel-Crafts catalysts may be used in this reaction. Typical examples are halogen compounds of metals or semimetals, for example, halogen compounds, organic halides or complexes of elements such as B, Al, Si, P, Ti, V, Fe, Zn, Mo, Sn, Sb, Te and W, or of oxygen element compounds such as PO, $SO_2$ and VO. More specific examples include $BF_3$, $BF_3O(C_2H_5)_2$, $BCl_3$, $AlCl_3$, $TiCl_4$, $SnCl_4$, $FeCl_3$, $WCl_5$, $POCl_3$, and $(C_2H_5)_3Al$.

There is no particular restriction on the reaction conditions (the details of this reaction are shown, for example, in C. Giordano, et al., SYNTHESIS, 92 (1971)).

(3) A method which comprises reacting the compound having a carbon-carbon unsaturated bond in the molecular chain with nitrile oxide, nitrile amine or nitrile ylide (known as a 1,3-dipole addition reaction), thereby performing N-alkylation.

For details of the 1,3-dipole addition reaction, see Huisgen, Angew. Chem., 75 604 (1863). The reaction of introducing an isooxazoline ring by nitrile oxide is described in Tada and Numata, et al., Journal of the Society of Rubber Industry, Japan 43, 996 (1970), and the reaction of introducing a pyrazoline ring by nitrile imine is disclosed in Caraculacu, et al. Polym. Lett. 6, 451 (1968).

(4) A method which comprises reacting the compound having a carbon-carbon unsaturated bond with a halohydroximino compound in the presence of a dehydrochlorinating agent such as anhydrous sodium carbonate, and as required, further reacting the product with an alkyl halide or dimethyl sulfate to perform N-methylation.

The halohydroximino compound can be obtained by reacting an alpha-haloaceto compound described in T. L. Gilchrist, et al., J. C. S. Chem. Commun., 1090 (1979) with hydroxylamine hydrochloride, or by reacting a vinyl compound such as acrolein, an acrylic acid ester or alpha-methylstyrene described in K. A. Ogloblin, et al., J. Org. Chem., U. S. S. R. 1, 1370 (1965) with nitrosil chloride.

The synthesis of a compound having an oxazine structure by the reaction of an olefin with a halohydroximino compound shown in a synthesis example hereinbelow was in accordance with the method of T. L. Gilchrist, et al., J. Chem. Soc. Perkin Trans. I 1275 (1983).

The synthesis of compounds having an oxazine structure is also described in detail in H. E. Zaugg, et al., Synthesis 85 (1984), Synthesis 182, (1984) and Synthesis 182 (1984).

The compounds having a heterocycle which are obtained by the above methods may be partly substituted by a substituent such as a halogen atom, a nitro group, an epoxy group, a carboxyl group or a hydroxy ether group.

(II) Other methods of producing compounds having a

bond in the molecule include a method which comprises reacting a living anion polymer having an alkaline metal and/or an alkaline earth metal at the ends obtained by polymerizing a monomer with a catalyst based on the alkali metal and/or alkaline earth metal (the so called anion polymerization catalyst) with the organic compound described hereinbelow, and then hydrolyzing the reaction product, and a method which comprises reacting a polymer obtained by adding the above metals to an unsaturated polymer having a double bond in the polymer chain or in a side chain by afterreaction, with the organic compound described hereinafter and hydrolyzing the reaction product (U.S. Pat. Nos. 4,550,142 and 4,647,625).

The polymerization catalyst used heretofore in anionic polymerization can be used as the above polymerization catalysts based on the above metals, and there is no particular restriction. Typical examples of the alkali metal-base catalysts include organic lithium compounds having 2 to 20 carbon atoms such as n-butyllithium and sec-butyllithium. Examples of the alkaline earth metal base catalysts are catalyst systems containing barium, strontium and calcium compounds disclosed in U.S. Pat. Nos. 3,946,385, 3,992,561, 4,079,176, 4,092,268, 4,112,210, 4,129,705, 4,260,519 and 4,297,240. The polymerization reaction and the reaction of adding an alkali metal and/or alkaline earth metal are carried out in hydrocarbon solvents heretofore used in anionic polymerizations or in solvents which do not destroy the above metal base catalysts, such as tetrahydrofuran, tetrahydropyran and dioxane. Examples of monomers that can be used in polymerization are the monomers which constitute the polymers or copolymers described hereinbelow. Examples of polymers used to add the above metals by after reaction are various diene (co)-polymers and partial hydrogenation products of these, and ethylene/propylene/diene monomer copolymers.

A preferred group of organic compounds which are used in reaction with the aforesaid polymers having the metals bonded thereto are shown below.

Compounds having a

bond in the molecule (in which X is an oxygen or sulfur atom) such as N-substituted lactams and the corresponding thiolactams such as N-methyl-beta-propiolactam, N-t-butyl-beta-propiolactam, N-phenyl-beta-propiolactam, N-methoxyphenyl-beta-propiolactam, N-naphthyl-beta-propiolactam, N-methyl-2-pyrrolidone, N-t-butyl-2-pyrrolidone, N-phenyl-3-pyrrolidone, N-methoxyphenyl-2-pyrrolidone, N-vinyl-2-pyrrolidone, N-benzyl-2-pyrrolidone, N-naphthyl-2-pyrrolidone, N-methyl-5-methyl-2-pyrrolidone, N-t-butyl-5-methyl-2-pyrrolidone, N-phenyl-5-methyl-2-pyrrolidone, N-methyl-3,3'-dimethyl-2-pyrrolidone, N-t-butyl-3,3'-dimethyl-2-pyrrolidone, N-phenyl-3,3'-dimethyl-2-pyrrolidone, N-methyl-2-piperidone, N-t-butyl-2-piperidone, N-phenyl-2-piperidone, N-methoxyphenyl-2-piperidone, N-vinyl-2-piperidone, N-benzyl-2-piperidone, N-naphthayl-2-piperidone, N-phenyl-3,3'-dimethyl-2-pyrrolidone, N-methyl-epsilon-caprolactam, N-phenyl-epsilon-caprolactam, N-methoxyphenyl-epsilon-caprolactam, N-vinyl-epsilon-caprolactam, N-benzyl-epsilon-caprolactam, N-naphthyl-epsilon-caprolactam, N-methyl-omega-laurolactam, N-phenyl-omega-laurolactam, N-t-butyl-omega-laurolactam, N-vinyl-omega-laurolactam and N-benzyl-omega-laurolactam; N-substituted cyclic ureas and the corresponding N-substituted thiocyclic ureas, such as 1,3-dimethyl-2-imidazolidinone, 1,3-diethyl-2-imidazolidinone, 1-methyl-3-ethyl-2-imidazolidinone, 1,3-dimethylethyleneurea, 1,3-diphenylethyleneurea, 1,3-di-t-butylethyleneurea and 1,3-divinylethyleneurea, and N-substituted aminoketones and the corresponding N-substituted aminothioketones, such as 4-dimethylaminobenzophenone, 4-diethylaminobenzophenone, 4-di-t-butylaminobenzophenone, 4-diphenylbenzophenone, 4,4'-bis(dimethylamino)benzophenone, 4,4'-bis(diethylamino)benzophenone, 4,4'-bis(di-t-butylamino)benzophenone, 4,4'-bis(diphenylamino)benzophenone, 4,4'-bis(-divinylamino)benzophenone, 4-dimethylaminoacetophenone, 4-diethylaminoacetophenone, 1,3-bis(diphenylamino)-2-propanone, and 1,7-bis(methylethylamino)-4-heptanone; and N-substituted aminoaldehydes and the corresponding N-substituted aminothioaldehydes, such as 4-dimethylaminobenzoaldehyde, 4-diphenylaminobenzoaldehyde and 4-divinylaminobenzaldehyde. The amount of these compounds to be used is preferably 0.05 to 10 moles per mole of the anion living polymer and the alkali metal and/or alkaline earth metal-base catalyst used at the time of bonding these metals by after-reaction. If it is less than 0.05 mole, the function of the resulting polyper as a dispersant is insufficient. If it exceeds 10 moles, the resulting polymer becomes difficult to dissolve in the medium because of a side reaction. The particularly preferred amount is 0.2 to 2 moles. The reaction usually proceeds for a period of several seconds to several hours at room temperature to 100° C. After the reaction, the desired polymer having the above functional group bonded thereto is recovered from the reaction solution by using a proton-donating solvent (such as water or an alcohol) to coagulate the resulting polymer, usually by steam stripping.

The above reaction is shown specifically by using 4,4'-bis(diethylamino)-benzophenone. In the formulae, P-Li represents an Li-terminated polymers and P represents a polymer chain.

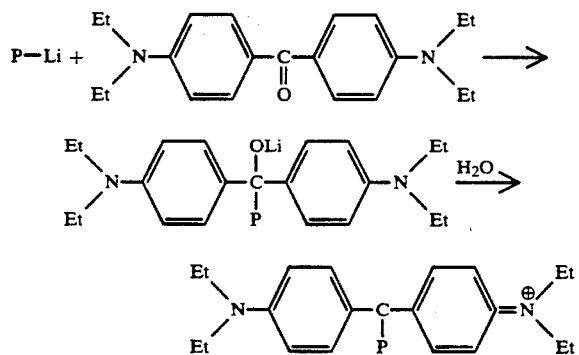

Especially preferred as the additive of this invention are conjugated diene polymers in which the above functional groups are bonded to one or both ends of the polymer chain. Specific examples include homopolymers and copolymers of conjugated dienes polymerizable with the above polymerization catalysts, such as butadiene, isoprene, 2,3-dimethylbutadiene, pentadiene and chloroprene; and copolymers of at least one conjugated diene with at least one monomer copolymerizable with it (for example, aromatic vinyl compounds such as styrene, vinyltoluene and alpha-methylstyrene, unsaturated nitrile compounds such as acrylonitrile and methacrylonitrile, unsaturated carboxylic acids such as acrylic acid, methacrylic acid, maleic acid and maleic anhydride, and unsaturated carboxylic acid esters such as methyl acrylate, ethyl acrylate, butyl acrylate and methoxyethyl acrylate). But the additive of this invention should not be limited to these examples, and suitable polymers (which dissolve in the medium or mutually dissolve with the medium) as the additives may be selected depending upon the type of the medium in which the inorganic or organic fine particles are to be dispersed. Likewise, there is no particular restriction on the molecular weight of these polymers, and they include compounds ranging from oligomers to higher molecular weight polymers (with a weight average molecular weight of about several hundred thousand). The optimum range of molecular weights may be selected depending upon the type of the media.

(III) The compounds having an oxazolinium ion are polymers (including oligomers) having an oxazolinium ion in the molecular chain or at the ends of the molecular chain. These polymers can be produced by polymerizing 2-oxazolines of the formula

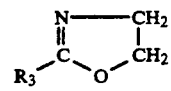

wherein $R_3$ is as defined above, with a cationic polymerization catalyst, and using a solvent having no nucleophilic reactivity as a polymerization stopper and a coagulating agent. If a solvent having nucleophilic reactivity, such as water, ammonia or a primary amine, is used as the polymerization stopper and the coagulating agent, an oxazolinium ion is not formed, but a hydroxyl group or a secondary amino group is formed. Thus, a polymer meeting the object of the invention cannot be obtained.

Typical examples of the 2-oxazolines are 2-oxazoline, 2-methyl-oxazoline, 2-ethyl-oxazoline and 2-substituted oxazolines having substituents other than methyl and ethyl may also be used if the substituents do not inhibit the polymerization reaction.

Ordinary cationic polymerization catalysts, such as p-toluenesulfonate esters, benzenesulfonate esters, methanesulfonate esters, trifluoromethanesulfonate esters, alkyl iodides, alkyl bromides, alkyl chlorides, benzyl bromides and benzyl chlorides may be used in this polymerization. There may also be used polymeric catalysts which dissolve in, or mutually dissolve with, the medium used in this invention. Examples of the latter include polymers having a proton-donating group such as a halogen atom, a sulfoxyl group or a phosphoxyl group, such as polyvinyl chloride, vinyl chloride/vinyl acetate copolymer, polyepichlorohydrin, epichlorohydrin/ethylene oxide copolymer, and a sulfoxyl group terminated polymer obtained by reacting a hydroxyl terminated polymer with p-toluenesulfonyl chloride.

Acetonitrile, benzonitrile, nitromethane, toluene and benzene may be among solvents that can be used in this polymerization.

The polymerization is carried out usually at −20° to 150° C., preferably 0° to 120° C.

By using a solvent having no nucleophilic reactivity, such as methanol, ethanol, diethyl ether, n-hexane and petroleum ether, as a polymerization stopper and a coagulating agent after the polymerization, a polymer having the desired oxazolinium ion is obtained. One example of the polymerization is shown as

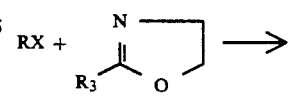

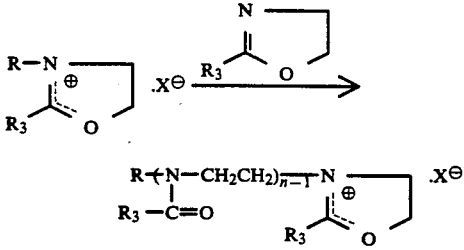

In these formulae, R represents a monovalent organic group, $R_3$ is as defined above, n represents a positive integer, and X represents an electrophilic group.

Details of this polymerization are disclosed, for example, in S. Kobayashi, et al., Encyclo. Polymer Sci. & Eng., Vol. 4 (2nd Ed.), 525 (1986).

The additive of this invention can be produced by the methods described above. The chemical structure of the backbone of compounds to which the aforesaid atomic groupings are bonded should be such that the compounds dissolve in, or mutually dissolve with, an organic medium or a thermoplastic polymer for which the additives of the invention are used. It may be selected according to the type of the medium. The molecular weight of the additive, which may vary depending upon the type of the medium, is usually 100 to 300,000 in weight average molecular weight (Mw).

At least one atomic grouping described hereinabove may be present in the molecule.

The particulate material for which the additives of the invention are used is an inorganic or organic substance. These may be in the form of a powder, flake or fiber. There is no particular limitation on the size of the particulate substance, and may usually be not more than 0.1 mm, preferably 0.01 to 50 micrometers.

Specific examples of the inorganic particulate substance include inorganic reinforcing materials such as metals, clay, carbon black, calcium carbonate, barium sulfate, silica, mica, glass and asbestos; metal compounds such as compounds of zinc, magnesium, lead and aluminum as reactive inorganic materials; inorganic pigments such as titanium dioxide, iron oxide and zinc chromate; inorganic fillers such as zinc oxide, magnesium oxide, antimony oxide, barium ferrite, strontium ferrite, beryllium oxide, pumice, aluminum hydroxide, magnesium hydroxide, basic magnesium carbonate, dolomite, calcium sulfate, ammonium sulfate, calcium sulfite, talc, mica, glass balloon, glass beads, glass fibers, calcium silicate, montmorillonite, bentonite, graphite, carbon fibers, molybdenum sulfide, boron fibers, silicon carbide fibers, zinc borate, barium meta-borate, and zirconium titanate; sludges precipitated from heavy oils during storage; carbon coming from the combustion chamber of an internal combustion engine into a lubricant oil within a crankcase; and sludges formed during use of a lubricant oil.

Specific examples of the organic particulate substance include low molecular weight organic compounds such as anthracene, pyrene and ferrocene; waxes precipitated at low temperatures; lubricant in oils or fuel oils; residues of distillation at atmospheric or reduced pressure of petroleum or naphtha and asphalthene; polycondensation products of imperfectly burned products of fuel oils which come into a lubricant oil in a crankcase from the combustion chamber of an internal combustion engine; organic pigments such as azo pigments, mordant dye-type lakes, phthalocyanine pigments and organic fluorescent pigments; fine particles of polyethylene, polystyrene, benzoguanamine resins, methacrylic acid resins, silicone resins, polyamide resins, polyester resins, polyphenylene oxide, polyphenylene sulfide, and phenolic thermosetting resins; and chops of fibers such as aramid fibers, polyamide fibers and polyester fibers.

Organic media for which the additives of this invention are useful include, for example, organic solvents such as benzene, toluene, hexane, cyclohexane, methyl ethyl ketone, acetone, methyl acetate and alcohols; polymerizable monomers (e.g. methyl methacrylate (for preparing methacrylate resin by cell casting method), styrene, vinyltoluene, methyl methacrylate, diarylphthalate, etc. (for preparing thermosetting unsaturated polyester resins)); base oils for lubricant oils (e.g. gasoline engine oils, diesel engine oils, gear oils, turbine oils, actuating oils, rubber incorporated oils (such as aromatic or naphthenic process oils and waxes)), such as mineral oil type base oils, and alpha-olefin type synthetic base oils or ester type synthetic oils; intermediate distillation petroleum fuel oils having a boiling point of 40° to 500° C. (such as gasoline, light oils, kerosene, diesel fuel oils, jet fuel oils and heavy oil); natural or synthetic waxes such as carnauba wax, montan wax, microcrystalline wax, paraffine wax, oxide wax, low molecular weight polyethylene wax, low molecular weight polypropyrene wax, and the like. These examples are not limitative.

Thermoplastic polymers for which the additives of the invention are useful include, for example, thermoplastic resins such as vinyl chloride resins, ABS resin, AS resin, polyethylene, polypropylene, polystyrene, high impact polystyrene, polyethylene terephthalate, polycarbonates, polyamides and polyphenylene ether; and elastomers and partial hydrogenation products of these, such as natural rubber, polyisoprene, polybutadiene, styrene/butadiene copolymer, acrylonitrile/butadiene copolymer, ethylene/propylene/ethylidenenorbornene copolymer, ethylene/propylene/diene copolymers, styrene/butadiene block copolymer, styrene/butadiene/styrene block copolymer, styrene/isoprene block copolymers, styrene/isoprene/styrene block copolymer and the like. These examples are not limitative. Thermosetting resins for which the additives of this invention are useful include, for example, unsaturated polyester resins, phenolic resins, xylene resins, urea resins, melamine resins, epoxy resins, silicone resins, alkyd resins, furan resins, and the like. These examples are not limitative. Partially modified thermosetting resins may also be used in this invention according to the purpose of use.

The additives of the invention are preferably added to prepolymers of the thermosetting resins. In the case of unsaturated polyester resins, prepolymers are added to the solution of the aforementioned polymerizable monomers.

The additives of the invention may be used singly or in combination. The amount of the additive may vary depending upon the type of the medium, or the content of the above-specified atomic grouping in the additive. Usually, it is at least 0.05 part by weight, preferably 0.1 to 50 parts by weight, especially preferably 0.5 to 20 parts by weight, per 100 parts by weight of the medium. In order to facilitate the solubility and the mixability of the additive in and with the medium, the additive preferably has a (weight average molecular weight)/(the number of the above-specified atomic grouping per molecule) value of not more than 200,000, more preferably not more than 10,000.

When the medium is a lubricant oil or a fuel oil, the additive is used normally in an amount of 0.01 to 20% by weight based on the oil.

For example, there are the following methods of using the additive.

(1) The additive is added in advance to an organic medium other than lubricant oils and fuel oils, or a thermoplastic polymer, and then the particulate substance is added.

(2) The additives are added together with the particulate substance to the organic medium, the thermoplastic polymer or the thermosetting resin.

(3) The particulate substance is added to the organic medium, the thermoplastic polymer or the thermosetting resin, and then the additive is added.

(4) The particulate substance is surface-treated in advance with the additive, and then added to the organic medium, the thermoplastic polymer or the thermosetting resin.

When the particulate substance surface-treated in advance with the additive is to be used, the amount of the additive for the surface treatment is usually at least 1% by weight, preferably at least 3% by weight, based on the particulate substance although it may vary depending upon the molecular weight of the additive, and the content of the above-specified atomic grouping.

The method of surface treating the particulate substance with the additive is not particularly limited. For example, the additive is dissolved in an inert organic solvent, and then the particulate substance is immersed in the resulting solution. Alternatively, a solution of the additive or a suspension of the additive in an insoluble medium such as water is coated with the substance. A dry blending method may also be applied.

When the medium is a thermoplastic polymer, the thermoplastic polymer should be mixed sufficiently with the particulate substance in order to produce a uniform dispersion of the particulate substance in the thermoplastic polymer by using the additive of the invention and the surface treated particulate substance. The preferred mixing conditions depend upon the type of the polymer.

It is possible to surface treat the particulate substance with the additive by using a kneader of an ordinary type, such as a Henschel mixer, a Banbury mixer, or a double concentric screw, and then mix the surface treated substance with the thermoplastic polymer.

Generally, a polymer is processed, for example, mixed under a high shear at a temperature far exceeding the second order transition temperature of the polymer, desirably at a temperature at which the polymer has a low melt viscosity. Accordingly, the processing of a thermoplastic polymer containing the additive of the invention is also carried out at the above temperature. Examples of the mixing apparatus are the aforesaid mixing machines, a two roll mill, and a Waring blender normally used for polymer processing.

The additive of this invention used to disperse a particulate substance uniformly in the thermoplastic polymer or the thermosetting resin should be a polymer having a backbone, or a monomer composition, compatible with the polymer or the monomer solution of the prepolymer. If its molecular weight is too low, the additive may bleed out onto the surface of the resulting shaped article. Preferably, the additive has a weight average molecular weight of 1,000 to 300,000. When the particulate substance is dispersed in an organic solvent for a paint or a magnetic fluid, the additive of this invention must be soluble in the organic solvent used, and the additive is selected according to the organic solvent. In this case, the additive has a preferable molecular weight of usually 100 to 10,000 in weight average molecular weight although it depends upon the amount of the additive used.

When the additive of this invention is used in a lubricant oil or a fuel oil, the additive should dissolve in these oils as in the above case. It should be a polymer having a backbone soluble in these oils.

The preferable weight average molecular weight of the additive is usually 1,000 to 100,000 although it depends also upon its amount when it is for fuel oils. For lubricant oils, its weight average molecular weight is usually preferably in the range of 1,000 to 100,000. When the additive of this invention is added to a lubricant oil, it also exhibits the function of a viscosity index improver, a low temperature flow modifying agent or an antioxidant. When the additive is to be added to a lubricant oil or a fuel oil, it is the general practice to first dissolve it in a diluent solvent which dissolves the additive, and then add the diluted additive to the oil and thereafter remove the solvent.

The additive of this invention facilitates the uniform dispersion of the particulate substances in organic media, in thermoplastic polymers or in thermosetting resin, and suppresses the rise of the viscosity of a system to which the particulate substance has been added. Accordingly, it offers a great advantage of markedly increasing the amount of the particulate substance.

Shaped articles of thermosetting resins having lower curing shrinkage and less internal stress than in the prior art, thereby inhibiting occurrence of defects, are produced by using prepolymers of the thermosetting resins to which the additives of the invention have been added.

The additive of this invention is multifunctional in that it imparts better low temperature flowability and detergent dispersibility as compared with the prior art, and to lubricant oils, it gives detergent dispersibility and increases the viscosity index.

The additives of this invention are useful, for example, as dispersing agents for a variety of materials such as magnetic materials for bonded magnets, magnetic recording materials (for toners, disks or tapes) or magnetic fluids, electrically conductive materials for paints, molded articles for EMI, fire retarding materials for cable coverings or building materials, pigments, fillers, reinforcing agents, catalysts, reflection preventing agents, dyes or FRTP, and also as detergent dispersing agents for lubricant oils or fuel oils.

The additives of this invention may also be used in the fields of paints, inks (printing inks, thermosensitive transfer inks), coating agents (a back-coating agent for a magnetic recording medium, a thermosensitive transfer ink ribon), adhesives and cosmetics.

The following Production Examples for the additives of the invention, Examples and Comparative Examples illustrate the invention further. It should be understood that the invention is not to be limited to these examples. In these examples, all parts and percentages are by weight unless otherwise specified.

The presence of $>\!C\!=\!N^{\oplus}\!<$ was determined by an ultraviolet light absorption spectrum at a wavelength of 310 to 315 nm, and an absorption spectrum of visible light at 360 nm. The presence of an oxazolinium ion was determined by an absorption spectrum of ultraviolet light at 310 nm and by peaks of 2.37, 2.47, 4.00, 4.43 and 7.45 ppm in an NMR spectrum.

PRODUCTION EXAMPLE 1

One mole of each of the olefins indicated in Table 1 and 300 ml of benzene were put in a vessel equipped with a stirrer, an internal heating device, a vapor condenser and a liquid solid feed inlet, and with stirring, they were heated to 60° C.

One mole of each reagent (1) and reagent (2) were added, and the mixture was reacted for about 1 hour.

The reaction solvent and the unreacted materials were removed by distillation at 90° C. and 300 mmHg.

Thus, additives A to C were obtained.

TABLE 1

| Additive | A | B | C |
|---|---|---|---|
| Compound having an unsaturated bond | 2-methyl-1-undecene | 1-eicosene | 7-tetradecene |
| Reagent (1) | benzylidene-butylamine and acetyl chloride | hydroxyl-benzamide | beta-bromo-hydroximino-ethylbenzene |
| Reagent (2) | tin tetrachloride | BF$_3$-ether complex | anhydrous sodium carbonate |
| Hetero ring | $>C=\overset{\oplus}{N}<$ | 1,3-oxazine structure | *1,3-oxazine structure |

PRODUCTION EXAMPLE 2

One hundred grams of each of the oligomers indicated in Table 2 was dissolved in 500 ml of cyclohexane. The solution was put in a vessel equipped with a stirrer, an internal heating device, a vapor condenser and a liquid-solid feed inlet. With stirring, it was heated to 60° C.

One mole of each of reagent (1) and reagent (2) were added, and the reaction was carried out for about 1 hour. Furthermore, 1.2 moles or reagent (3) was added and reacted.

A small amount of methanol was added to stop the reaction, and the reaction mixture was poured into 1 liter of acetone/methanol (50/50) to coagulate the product. The product was dried by a vacuum dryer.

Thus, additives D to F of the invention were obtained.

TABLE 2

| Additive | D | E | F |
|---|---|---|---|
| Compound having a unsaturated bond | liquid isoprene (Mw = 4000) | styrene/butadiene block copolymer (Mw = 70000) | ethylene/propylene/diene copolymer (Mw = 100000) |
| Reagent (1) | benzilidene stearylamine benzoyl chloride | N-hydroxymethyl-thiobenzamide | alpha-chloro-hydroxyimino propanal |
| Reagent (2) | titanium tetrachloride | tin tetrachloride | triethylamine |
| Reagent (3) | — | — | benzyl chloride |
| Hetero ring | $>C=\overset{\oplus}{N}<$ | 1,3-oxazine structure | $>C=\overset{\oplus}{N}<$ |

EXAMPLE 1

The effect of additives A, B, D and F obtained in Production Examples 1 and 2 to inhibit flocculation of inorganic fine particles dispersed in toluene was examined.

In each run, the dispersing effect of the additive was evaluated by the ratio of the average particle diameter (median diameter) of the additive dispersed by ultrasonication to that of the additive measured 10 minutes after the ultrasonication was stopped. The average particle size (micrometers) was measured by using a laser diffraction type particle size meter (SK LASER MICRON SIZER PRO-700, supplied by Seishin Co., Ltd.). The measuring conditions of the average particle diameter were as follows:

Amount of the inorganic fine particles: 50–100 mg
Amount of toluene: 300 ml

The ratio $(D_{50})_{10}/(D_{50})_0$ of the average particle diameter 10 minutes after stopping ultrasonication, $(D_{50})_{10}$, to the average particle diameter of the inorganic fine particles 0 minute after stopping ultrasonication $(D_{50})_0$, was defined as the degree of flocculation. $D_{50}$ is the particle diameter for 50% of the cumulative distribution of the particle diameters.

The results for various inorganic fine particles are shown in Tables 3 and 4. The amounts of the additives used are expressed as % by weight based on the inorganic fine particles.

TABLE 3

| Run No. | Inorganic fine particles | Degree of flocculation ($\mu m$) | none 0 | A 5% | B 5% |
|---|---|---|---|---|---|
| 1 | carbon black (HAF) (*1) | $[D_{50}]_0$ | 1.1 | 1.1 | 1.1 |
|   |   | $[D_{50}]_{10}$ | 9.5 | 1.0 | 4.5 |
|   |   | $\frac{[D_{50}]_{10}}{[D_{50}]_0}$ | 8.64 | 0.91 | 4.09 |
| 2 | zinc oxide (*2) | $[D_{50}]_0$ | 2.0 | 2.0 | 2.0 |
|   |   | $[D_{50}]_{10}$ | 8.5 | 2.3 | 5.3 |
|   |   | $\frac{[D_{50}]_{10}}{[D_{50}]_0}$ | 4.25 | 1.15 | 2.65 |
| 3 | alumina (*3) | $[D_{50}]_0$ | 5.0 | 5.0 | 5.0 |
|   |   | $[D_{50}]_{10}$ | 12.5 | 5.1 | 8.1 |
|   |   | $\frac{[D_{50}]_{10}}{[D_{50}]_0}$ | 2.50 | 1.02 | 1.62 |
| 4 | calcium carbonate (*4) | $[D_{50}]_0$ | 7.8 | 7.8 | 7.8 |
|   |   | $[D_{50}]_{10}$ | 23.0 | 7.6 | 16.5 |
|   |   | $\frac{[D_{50}]_{10}}{[D_{50}]_0}$ | 2.95 | 0.97 | 2.12 |

(*1): Asahi #70, a product of Asahi Carbon Co., Ltd.
(*2): Active zinc chemical, a product of Seido Chemical Co., Ltd.
(*3): "Higirite A-34", a product of Japan Light Metal Co., Ltd.
(*4): NS #100, a product of Nitto Powderization Co., Ltd.

TABLE 4

| Run No. | Inorganic fine particles | Degree of flocculation ($\mu$m) | Additive none 0% | D 0.1% | D 1.0% | D 5.0% | F 0.1% | F 1.0% | F 5.0% |
|---|---|---|---|---|---|---|---|---|---|
| 5 | Ferrite powder (*5) | $[D_{50}]_0$ | 2.0 | 2.0 | 2.0 | 2.0 | 2.0 | 2.0 | 2.0 |
|   |   | $[D_{50}]_{10}$ | 16.0 | 8.2 | 3.5 | 1.8 | 11.0 | 8.5 | 2.5 |
|   |   | $\dfrac{[D_{50}]_{10}}{[D_{50}]_0}$ | 8.0 | 4.10 | 1.75 | 0.90 | 5.50 | 4.25 | 1.25 |
| 6 | Cupric oxide (*6) | $[D_{50}]_0$ | 1.2 | 1.2 | 1.2 | 1.2 | 1.2 | 1.2 | 1.2 |
|   |   | $[D_{50}]_{10}$ | 7.3 | 7.0 | 5.6 | 1.8 | 7.3 | 6.4 | 5.2 |
|   |   | $\dfrac{[D_{50}]_{10}}{[D_{50}]_0}$ | 6.08 | 5.83 | 4.67 | 1.50 | 6.08 | 5.33 | 4.33 |
| 7 | Glass powder (*7) | $[D_{50}]_0$ | 10.3 | 10.3 | 10.3 | 10.3 | 10.3 | 10.3 | 10.3 |
|   |   | $[D_{50}]_{10}$ | 12.5 | 12.3 | 11.5 | 10.3 | 12.3 | 12.0 | 10.9 |
|   |   | $\dfrac{[D_{50}]_{10}}{[D_{50}]_0}$ | 1.21 | 1.19 | 1.12 | 1.00 | 1.19 | 1.17 | 1.06 |

(*5): Average particle diameter obtained by an electron microscope.
(*6): A product of Nisshin Chemical Co., Ltd.
(*7): PFA001, a product of Nitto Boseki Co., Ltd.

The results given in Tables 3 and 4 clearly show that the additives of the invention prevent flocculation of inorganic fine particles and are effective for dispersing them stably.

By increasing the amounts of the additives, their effects further increase.

EXAMPLE 2

Any of the additives A to F of the invention was added to a naphthenic process oil (Diana Process Oil NM-280, a product of Idemitsu Industries, Co., Ltd.) or toluene, and its effect on the viscosity was examined. The inorganic particles used were calcium carbonate NS#100, (a product of Nitto Powderization Co., Ltd.), clay (NN Kaolin Clay produced by Tsuchiya Kaolin Kogyo Co., Ltd.), silica (Hi-Sil), (a product of Pittsburgh Plate Glass Co.), HAF carbon black (Asahi #70, a product of Asahi Carbon Black Co.), talc (HITRON, a product of Takehara Chemical Industry Co.), and titanium dioxide (Tipaque R-650, a product of Ishihara Sangyo Kaisha, Ltd.). The results are shown in Table 5.

TABLE 5

| | Run No. 8 | 9 | 10 | 11 | 12 | 13 | 14 | 15 |
|---|---|---|---|---|---|---|---|---|
| Calcium carbonate (parts) | 35 | 50 | | | | | | |
| Carbon black (parts) | | | 15 | 25 | 35 (*8) | | | |
| Silica (parts) | | | | | | 10 | 20 | |
| Clay (parts) | | | | | | | | 30 |
| Talc (parts) | | | | | | | | |
| Zinc oxide (parts) | | | | | | | | |
| Titanium oxide (parts) | | | | | | | | |
| Naphthenic oil (parts) | 65 | 50 | 85 | 75 | 65 (*9) | 90 | 80 | 70 |
| Toluene (parts) | | | | | | | | |
| Additive (parts) | | | | | | | | |
| A | 0.5 | 0.5 | | | | | | 1.0 |
| B | | | | | | 1.5 | | |
| C | | | | | | | 3.0 | 3.0 |
| D | | | 7.0 | 7.0 | | | | |
| F | — | | | | | | | |
| B-type viscosity (25° C., cps) | 430 (2300) | 5600 (35500) | 1100 (1900) | 8300 (22500) | 31000 (95000) | 120 (530) | 7400 (11600) | 330 (32000) |

| | Run No. 16 | 17 | 18 | 19 | 20 | 21 | 22 |
|---|---|---|---|---|---|---|---|
| Calcium carbonate (parts) | | | | | | | |
| Carbon black (parts) | | | | | | | |
| Silica (parts) | | | | | | | |
| Clay (parts) | 50 | | | | | | |
| Talc (parts) | | 20 | 40 | | | | |
| Zinc oxide (parts) | | | | 50 | 50 | | |
| Titanium oxide (parts) | | | | | | 30 | 50 |
| Naphthenic oil (parts) | 50 | 80 | 60 | 50 (*9) | | 70 (*9) | |
| Toluene (parts) | | | | | 50 | | 50 |
| Additive (parts) | | | | | | | |
| A | 1.0 | | | | | | 1.5 |
| B | | | | | | | |
| C | | | | | | 2.5 | |
| D | | | | | 2.5 | | |
| F | | 5.0 | 5.0 | 2.5 | | | |
| B-type viscosity | 2300 | 1100 | 4700 | 43000 | 33000 | 19000 | 2600 |

TABLE 5-continued

| (25° C., cps) | (98000) | (2800) | (12000) | (85000) | (98000) | (67000) | (10000) |
|---|---|---|---|---|---|---|---|

Note:
The parenthesized figures are B-type viscosity measured in the absence of the additive.
(*8): FEF carbon black (Seast SO), a product of Tokai Carbon Co., Ltd.,
(*9): Flex M, a product of Fuji Kosan Co., Ltd.

It is seen from Table 5 that by using the additives of this invention, dispersions having a substantially reduced B-type viscosity can be obtained. The marked decrease in viscosity can be noted in the case of calcium carbonate, carbon black, clay, titanium oxide and talc.

The decrease of viscosity in the dispersions makes it easy to mix the inorganic fillers with organic substances, and reduce the amount of energy required during mixing.

PRODUCTION EXAMPLE 3

One mole of each of the alpha-olefins or polybutene indicated in Table 6 and 200 ml of benzene were put in a vessel equipped with a stirrer, an internal heating device, a vapor condenser, and a liquid solid feed inlet.

One mole each of reagent (1) and reagent (2) shown in Table 6 were added, and the reaction was carried out for about 1 hour. Methanol was added to stop the reaction. Furthermore, 500 to 1 liter of methanol was added. The reaction mixture was then cooled in a refrigerator.

The precipitate obtained was washed with methanol and dried. Thus, additives G to J were obtained.

TABLE 6

| Additive | G | H | I | J |
|---|---|---|---|---|
| Compound having an unsaturated bond at the ends | α-olefin (*10) $CH_3\text{-}(CH_2)_{14}CH=CH_2$ | α-olefin (*11) $CH_3\text{-}(CH_2)_{20}CH=CH_2$ | polybutene (Mw 1000) | polybutene (Mw 300) |
| Reagent (1) | benzylidene butylamine | benzylidene stearylamine | benzylidene octylamine | benzylidene methylamine |
| Reagent (2) | acetyl chloride tin tetrachloride | benzoyl chloride antimony pentachloride | acetyl chloride titanium tetrachloride | propionyl chloride tin chloride |

(*10) DIALENE 168; a $C_{13}$-$C_{18}$ mixture, a product of Mitsubishi Kasei Corp.
(*11) DIALENE 208; a $C_{20}$-$C_{28}$ mixture, a product of Mitsubishi Kasei Corp.

PRODUCTION EXAMPLE 4

One hundred grams of each of the oligomers or the low molecular weight polymers shown in Table 7 was dissolved in 500 ml of benzene or dichloromethane. The solution was put in a vessel equipped with a stirrer, an internal heating device, a vapor condenser and a liquid solid feed inlet. With stirring, the solution was heated to 60° C.

One mole each of the reagent (1) and reagent (2) were added and the mixture was reacted for about 1 hour. Furthermore, 2.0 moles of the reagent (3) was added and reacted.

After the reaction, the reaction mixture was poured into 1 liter of methanol to coagulate the product completely. The resulting liquid product was dried in a vacuum dryer.

Thus, additives K to N were obtained.

TABLE 7

| Additive | K | L |
|---|---|---|
| Compound having an unsaturated bond at the ends | α-olefin oligomer (*12) $CH_3\text{-}(CH\text{-}CH_2)_n\text{-}CH=CH_2$ <br> \| <br> R | polystyrylethyl methacrylate (*13) $C_4H_9\text{-}(CH_2\text{-}CH)_n\text{-}CH_2CH_2OOCC=CH_2$ <br> \| \| <br> (phenyl) $CH_3$ |
| Reagent (1) |  (phenyl)-CONHCH$_2$OH | 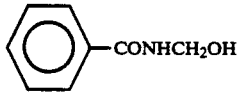 HOOC-(phenyl)-C(Cl)=N-OH |
| Reagent (2) | Boron trifluoride etherate | Triethylamine |
| Reagent (3) | Benzyl chloride | Chloromethyl ether |

(*12): Lipolube 400, molecular weight 800, a product of Lion K.K.
(*13): CHEMLINK 4500B, molecular weight 13,000, a product of Somar Corp.

| Additive | M | N |
|---|---|---|
| Compound having an unsaturated bond at the ends | polyethylene glycol dimethacrylate (*14) <br> $O\text{-}(CH_2CH_2O)_n\text{-}OOC\text{-}C(CH_3)=CH_2$ <br> \| <br> $O$ <br> \| <br> $C\text{-}C(CH_3)=CH_2$ | polyisobutlylene (*15) <br> $R\text{-}(CH_2\text{-}C(CH_3)_2)_n\text{-}C(CH_3)=CH_2$ |

TABLE 7-continued

Reagent (1):

$$\text{Ph-C(Cl)=N-NH-Ph-Ph-C(Cl)=N-CH}_2\text{COOCH}_3$$

| | | |
|---|---|---|
| Reagent (2) | Pyridine | Triethylamine |
| Reagent (3) | Dimethyl sulfate | Dimethyl sulfate |

(*14): NK ester-23G, n = 23, a product of Shin-Nakamura Chemical K.K.
(*15): Tetrax-3T, molecular weight 30,000, a product of Nesseki Chemical Co., Ltd.

EXAMPLE 3

In the same way as in Example 1, the effect of the additives G, I and J to inhibit flocculation of inorganic fine particles dispersed in toluene was examined.

The results are shown in Table 8. The amounts of the additives are shown by % by weight based on the inorganic substance.

The results given in Table 8 clearly show that the additives of this invention prevent flocculation of the inorganic fine particles and stabilize their dispersion. It is also seen that by increasing the amount of the additives, this effect is correspondingly increased.

or carbon black in the naphthenic process oil. Thus, the mere addition of the additives of the invention gives an effect of inhibiting the rising of the viscosity without requiring the addition of water or heating.

EXAMPLE 5

Aluminum hydroxide (Higirite A-34, a product of Japan Light Metals Co., Ltd.) was dispersed in polyisoprene rubber (cis-1,4=98%, Nipol IR-2200, a product of Nippon Zeon Co., Ltd.) by using a small sized kneader (Bravender Plastograph). The effect of the additive H on the viscosity of the dispersion was examined. The results are shown in Table 10.

TABLE 8

| Run No. | Inorganic fine particles | Degree of flocculation (μm) | Additive G 0% | G 10% | I 0% | I 10% | I 20% | J 10% | J 20% |
|---|---|---|---|---|---|---|---|---|---|
| 23 | Carbon black (HAF) | $[D_{50}]_0$ | 1.1 | 1.1 | | | | | |
| | | $[D_{50}]_{10}$ | 13 | 0.9 | | | | | |
| | | $\frac{[D_{50}]_{10}}{[D_{50}]_0}$ | 11.8 | 0.82 | | | | | |
| 24 | Titanium dioxide | $[D_{50}]_0$ | 2.1 | 2.2 | | | | | |
| | | $[D_{50}]_{10}$ | 35 | 2.3 | | | | | |
| | | $\frac{[D_{50}]_{10}}{[D_{50}]_0}$ | 16.7 | 1.05 | | | | | |
| 25 | Magnetic powder (*16) | $[D_{50}]_0$ | | | 1.8 | 1.8 | 1.8 | 1.9 | 1.9 |
| | | $[D_{50}]_{10}$ | | | 21 | 2.3 | 1.8 | 2.0 | 1.9 |
| | | $\frac{[D_{50}]_{10}}{[D_{50}]_0}$ | | | 11.7 | 1.28 | 1.00 | 1.05 | 1.00 |

(*16): BL-200, a product of Titan Kogyo K.K.

EXAMPLE 4

The effect of the additive K or L on the viscosity of a naphthenic process oil (Diana Process Oil NM-280, a product of Idemitsu Industries, Co., Ltd.) in which titanium dioxide (Tipaque R-650, a product of Ishihara Sangyo Kaisha, Ltd.) or carbon black (Seast SO, FEF, a product of Tokai Carbon Co., Ltd.) was dispersed was examined. The results are shown in Table 9.

TABLE 9

| | Run No. 26 | Run No. 27 |
|---|---|---|
| Titanium dioxide (parts) | 40 | |
| Carbon Black (parts) | | 35 |
| Naphthenic oil (parts) | 60 | 65 |
| Additive (parts) | | |
| K | 2 | |
| L | | 1.5 |
| B-type viscosity (25° C., cps) | 96400 (134000) | 31000 (95000) |

The use of the additives of this invention markedly reduced the viscosity of a dispersion of titanium dioxide

TABLE 10

| | Run No. 28* | Run No. 29 |
|---|---|---|
| Aluminum hydroxide (parts) | 100 | 100 |
| Polyisoprene rubber (parts) | 100 | 100 |
| Additive H (parts) | — | 10 |
| Compound Mooney viscosity ($ML_{1+4}$, 100° C.) | 63 | 51 |

*Comparison

The results show that the addition of the additives resulted in the decrease of the Mooney viscosity of the compound by 19%.

EXAMPLE 6

Talc (Hitron, a product of Takehara Chemical Industry Co., Ltd.) or silica (Hi-sil 233, a product of Pittsburgh Plate Glass Co.) was dispersed in ethylene/propylene copolymer (Esprene, a product of Sumitomo Chemical Co., Ltd.) by using a small-sized kneader (Bravender Plastograph). The effect of the additives M and N on the viscosity of the compound was examined.

TABLE 11

|  | Run No. | | | |
| --- | --- | --- | --- | --- |
|  | 30 (*) | 31 | 32 (*) | 33 |
| Ethylene/propylene copolymer Rubber (parts) | 100 | 100 | 100 | 100 |
| Talc (parts) | 100 | 100 | | |
| Silica (parts) | | | 75 | 75 |
| Additives (parts) | | | | |
| M | 0 | 10 | | |
| N | | | 0 | 15 |
| Compound Mooney viscosity (ML$_{1+4}$, 100° C.) | 95 | 81 | 124 | 101 |

(*) Comparative Example.

The effect of the additives of the invention to inhibit the rise of the viscosity can be clearly noted from the results shown in Tables 10 and 11.

PRODUCTION EXAMPLE 5

By the same procedure as in the production of the additive D except that a hydrogenation product of a (styrene/butadiene=22/78, weight average molecular weight 70,000, iodine value 20) was used instead of the liquid polyisoprene. Thus, additive O was produced.

EXAMPLE 7

20 to 300 mg of organic fine particles (fine particles of nylon 12 having an average particle diameter of 7.4 micrometers or fine particles of polyethylene terephthalate (PET) having an average particle diameter of 11.5 microns) was dispersed in 300 ml of toluene using the additive F or O. The effect of the additive to inhibit flocculation of the organic fine particles was evaluated as in Example 1. The amount of the additive used was 5% based on the organic fine particles. The results are shown in Table 12.

TABLE 12

| Run No. | Organic fine particles | Degree of flocculation | Additive | | | |
| --- | --- | --- | --- | --- | --- | --- |
| | | | F | | O | |
| | | | 0% | 5% | 0% | 5% |
| 34 | Nylon 12 | [D$_{50}$]$_0$ | 7.4 | 7.3 | | |
| | | [D$_{50}$]$_{10}$ | 34.3 | 8.1 | | |
| | | $\frac{[D_{50}]_{10}}{[D_{50}]_0}$ | 4.6 | 1.2 | | |
| 35 | PET | [D$_{50}$]$_0$ | | | 11.3 | 11.7 |
| | | [D$_{50}$]$_{10}$ | | | 30.4 | 12.1 |
| | | $\frac{[D_{50}]_{10}}{[D_{50}]_0}$ | | | 2.7 | 1.0 |

PRODUCTION EXAMPLE 6

Acetonitrile (6 ml), 1.98 g (20 mmol) of 2-ethyl-2-oxazoline and 0.186 g (1 mmol) of methyl p-toluenesulfonate were charged in a 230 ml glass vessel under a dry nitrogen. The temperature was returned to room temperature, and the solvent was evaporated. The residue was extracted with chloroform, and the extract was concentrated. It was then reprecipitated by using 150 ml of n-hexane to give 2.01 g (yield 97%) of a white powdery polymer (additive P).

After the same polymerization as above was carried out, 0.54 g of water and 1.7 g of potassium carbonate as 24 hours. Then, the solvent was removed by evaporation. The residue was extracted from chloroform. The extract was concentrated and again precipitated with 150 ml of n-hexane to give 0.81 g of a white powdery polymer (additive P').

PRODUCTION EXAMPLE 7

A polyolefin containing hydroxyl groups at both ends (Epol, a product of Idemitsu Petrochemical Co., Ltd.) was coagulated and purified by using benzene-methanol and then a portion (0.25 mol) of it was put into a 1-liter three-necked flask, and dissolved in 500 ml of benzene. 0.14 mole of p-toluenesulfonyl chloride was added, and at 15° C. or below, 80 ml of a 5N aqueous solution of sodium hydroxide was added dropwise. Subsequently, 0.14 mole of p-toluenesulfonyl chloride and 50 ml of a 5N aqueous solution of sodium hydroxide were added. The organic layer (benzene layer) was separated, washed with a 10% aqueous solution of sodium hydroxide, and dried over anhydrous sodium carbonate. The solvent was removed to give a polyolefin containing a tosylate group at both ends (yield 89%).

17 mmoles of the tosylate-terminated polyolefin, 38 mmoles of 2-methyl-2-oxazoline and 50 ml of benzene were put in a 100 ml flask, and polymerized at 60° C. for 13 hours. The temperature returned to room temperature, and then, the contents of the flask were poured into 200 ml of methanol and coagulated. The yield of the polymer obtained (additive Q) was 96%.

PRODUCTION EXAMPLE 8

Polyepichlorohydrin (Gechron 1000, a product of Nippon Zeon Co., Ltd.) was coagulated and purified with benzene-methanol. After sufficient drying, this polymer was used in a reaction of introducing an oxazolinium ion.

A 100 ml glass vessel under a dry nitrogen atmosphere was charged with 50 ml of benzene, 10 mmol of 2-methyl-2-oxazoline and 7 mmols of the purified polyepichlorohydrin, and they were reacted at 80° C. for 8 hours. The temperature was returned to room temperature, and the reaction mixture was poured into 200 ml of methanol (additive R).

EXAMPLE 8

The effect of the additives of this invention P to R and the starting materials (comparative additives P' to R') to inhibit flocculation of various inorganic fine particles dispersed in methyl ethyl ketone was examined. The amount of the inorganic fine particles was 50 to 100 mg, and the amount of methyl ethyl ketone was 300 ml. The results are shown in Table 13.

The inorganic fine particles used were carbon black (MA 100, a product of Mitsubishi Kasei Corp.) titanium dioxide (Tipaque R-660) and a glass powder (PKFA-001, a product of Nitto Boseki Co., Ltd.). The amounts of the additives were 6 or 10% based on the inorganic particles.

The results given in Table 13 clearly show that the additives of this invention prevent flocculation of the inorganic fine particles and have an effect of stabilizing their dispersion.

TABLE 13

|  | Run No. | | | | | |
| --- | --- | --- | --- | --- | --- | --- |
|  | 36 | 37 (*) | 38 | 39 (*) | 40 | 41(*) |
| Inorganic fine particles | Carbon black | | Titanium dioxide | | Glass powder | |
| Additive | P | P' | Q | Q' | R | R' |

TABLE 13-continued

| | Run No. | | | | | |
|---|---|---|---|---|---|---|
| | 36 | 37 (*) | 38 | 39 (*) | 40 | 41(*) |
| Amount (%) | 5% | 5% | 5% | 5% | 10% | 10% |
| $[D_{50}]_0$ (μm) | 1.1 | 1.1 | 1.7 | 2.0 | 11 | 11 |
| $[D_{50}]_{10}$ (μm) | 0.8 | 9.8 | 1.9 | 34.0 | 11 | 23 |
| $\frac{[D_{50}]_0}{[D_{50}]_{10}}$ | 0.7 | 8.9 | 1.1 | 17.0 | 1.0 | 2.1 |

(*) Comparison

EXAMPLE 9

The effect of the additives of the invention to inhibit flocculation of various organic fine particles dispersed in toluene was evaluated as in Example 1. The amount of the organic fine particles was 100 to 150 mg, and the amount of toluene was 300 ml.

The results are shown in Table 14.

The organic fine particles used were benzoguanamine fine particles (Epostar, a product of Japan Catalytic Chemical Co., Ltd.), and methacrylate resin fine particles (MP, a product of Soken Chemical Co., Ltd.). The amounts of the additives used were 3% based on the organic fine particles.

The results given in Table 14 clearly show that the additives of this invention prevent flocculation of the organic fine powders, and have an effect of stabilizing their dispersion.

TABLE 14

| | Run No. | | | |
|---|---|---|---|---|
| | 42 | 43 (*) | 44 | 45 (*) |
| Organic fine particles | benzoguanamine resin particles | | methacrylate particles | |
| Additive | Q | Q' | R | R' |
| $[D_{50}]_0$ (μm) | 1.1 | 1.2 | 13.5 | 13.6 |
| $[D_{50}]_{10}$ (μm) | 1.3 | 12.1 | 14.1 | 94.5 |
| $\frac{[D_{50}]_{10}}{[D_{50}]_0}$ | 1.2 | 10.1 | 1.0 | 6.9 |

(*) Comparison

PRODUCTION EXAMPLE 9

A 2-liter stainless steel polymerization vessel was washed, dried and purged with dry nitrogen and 50 g of 1,3-butadiene, 100 g of styrene, 820 g of benzene, 0.5 millimole of diethylene glycol dimethyl ether and the amount indicated in Table 15 of an n-hexane solution of n-butyl lithium were added. With stirring, the monomers were polymerized at 60° C. for 2 hours. After the polymerization, each of the modifiers indicated in Table 15 was added, and the mixture was stirred for 30 minutes. The polymer solution in the polymerization reactor was transferred to a 2.0% methanol solution of 2,6-di-t-butyl-p-cresol to coagulate the resulting polymer. It was then dried at 60° C. under reduced pressure for 24 hours.

As a result, additives S to V and V' were obtained.

The amount of styrene was determined by an infrared spectrophotometer (Hampton, Anal. Chem., 21, 923 (1949)). The weight average molecular weights of the additives were measured by gel permeation chromatography under the following conditions (calculated for standard polystyrene).

TABLE 15

| Additive | n-butyl lithium (millimole) | Modifier | | Structure | |
|---|---|---|---|---|---|
| | | Compound | millimole | Amount of styrene (%) | Weight average molecular weight |
| S | 1.3 | 4,4'-bis(diethylamino)benzophenone | 1.5 | 66 | $155 \times 10^3$ |
| T | 30 | 4,4'-bis(diethylamino)benzophenone | 35 | 68 | $5 \times 10^3$ |
| U | 0.5 | 4,4'-bis(diethylamino)benzophenone | 0.8 | 66 | $810 \times 10^3$ |
| V | 1.3 | N-methyl-2-pyrrolidone | 1.5 | 67 | $160 \times 10^3$ |
| V' | 1.3 | — | — | 68 | $170 \times 10^3$ |

EXAMPLE 10

The effect of the additives S-V and V' (comparison) on the dispersion of particulate substances in toluene was evaluated as in Example 1. The results are shown in Table 16.

The inorganic fine particles used were the same carbon black, zinc oxide, alumina and calcium carbonate as used in Example 1. The organic fine particles were the nylon 12 and PET used in Example 8.

| Measuring conditions | |
|---|---|
| Inorganic fine particles | 50 to 100 mg |
| Toluene | 350 ml |
| Organic fine particles | 20 to 300 mg |
| Toluene | 300 ml |

The amount of the additive used is expressed by % by weight based on the particulate substance.

TABLE 16

| Run No. | Fine particles | Degree of flocculation (μm) | None | S | | | T | | | U | | | V | | | V' | | |
|---|---|---|---|---|---|---|---|---|---|---|---|---|---|---|---|---|---|---|
| | | | 0% | 0.1% | 1.0% | 5.0% | 0.1% | 1.0% | 5.0% | 0.1% | 1.0% | 5.0% | 0.1% | 1.0% | 5.0% | 0.1% | 1.0% | 5.0% |
| 46 | Carbon black | $[D_{50}]_0$ | 1.1 | 1.1 | 1.1 | 1.1 | 1.1 | 1.1 | 1.1 | 1.1 | 1.1 | 1.1 | 1.1 | 1.1 | 1.1 | 1.1 | 1.1 | 1.1 |
| | | $[D_{50}]_{10}$ | 9.5 | 1.2 | 1.1 | 1.1 | 1.3 | 1.1 | 1.1 | 4.5 | 3.0 | 2.8 | 1.2 | 1.1 | 1.1 | 9.5 | 9.3 | 9.2 |
| | | $\frac{[D_{50}]_{10}}{[D_{50}]_0}$ | 8.64 | 1.09 | 1.00 | 1.00 | 1.18 | 1.00 | 1.00 | 4.09 | 2.73 | 2.55 | 1.09 | 1.00 | 1.00 | 8.64 | 8.45 | 8.36 |
| 47 | Zinc oxide | $[D_{50}]_0$ | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 | 2.0 |
| | | $[D_{50}]_{10}$ | 8.5 | 2.9 | 2.7 | 2.5 | 2.7 | 2.4 | 2.3 | 6.5 | 5.1 | 4.1 | 2.5 | 2.3 | 2.2 | 8.6 | 8.5 | 8.3 |

TABLE 16-continued

| | | | | | | | | | | | | | | | | | | |
|---|---|---|---|---|---|---|---|---|---|---|---|---|---|---|---|---|---|---|
| | | $\frac{[D_{50}]_{10}}{[D_{50}]_0}$ | 4.25 | 1.45 | 1.35 | 1.25 | 1.35 | 1.20 | 1.15 | 3.25 | 2.55 | 2.05 | 1.25 | 1.15 | 1.10 | 4.30 | 4.25 | 4.15 |
| 48 | Alumina | $[D_{50}]_0$ | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| | | $[D_{50}]_{10}$ | 12.5 | 7.9 | 6.9 | 5.5 | 7.5 | 6.1 | 5.1 | 12.5 | 10.5 | 8.2 | 7.6 | 6.4 | 5.0 | 13.0 | 13.0 | 12.5 |
| | | $\frac{[D_{50}]_{10}}{[D_{50}]_0}$ | 2.50 | 1.96 | 1.38 | 1.10 | 1.50 | 1.22 | 1.05 | 2.05 | 2.10 | 1.84 | 1.52 | 1.28 | 1.00 | 2.60 | 2.60 | 2.5 |
| 49 | Calcium carbonate | $[D_{50}]_0$ | 7.8 | 7.8 | 7.8 | 7.8 | 7.8 | 7.8 | 7.8 | 7.8 | 7.8 | 7.8 | 7.8 | 7.8 | 7.8 | 7.8 | 7.8 | 7.8 |
| | | $[D_{50}]_{10}$ | 23.0 | 11.0 | 9.3 | 8.1 | 10.3 | 8.5 | 7.7 | 21.5 | 16.5 | 12.3 | 10.9 | 9.3 | 7.9 | 23.5 | 23.0 | 22.5 |
| | | $\frac{[D_{50}]_{10}}{[D_{50}]_0}$ | 2.95 | 1.41 | 1.19 | 1.04 | 1.32 | 1.09 | 0.90 | 2.76 | 2.12 | 1.58 | 1.40 | 1.19 | 1.01 | 3.01 | 2.95 | 2.88 |
| 50 | Nylon 12 | $[D_{50}]_0$ | 7.4 | | | 7.6 | | | | | | | | | | | | |
| | | $[D_{50}]_{10}$ | 34.3 | | | 8.8 | | | | | | | | | | | | |
| | | $\frac{[D_{50}]_{10}}{[D_{50}]_0}$ | 4.64 | | | 1.16 | | | | | | | | | | | | |
| 51 | PET | $[D_{50}]_0$ | 11.5 | | | | | | | | | | | | | 11.9 | | |
| | | $[D_{50}]_{10}$ | 30.7 | | | | | | | | | | | | | 12.4 | | |
| | | $\frac{[D_{50}]_{10}}{[D_{50}]_0}$ | 2.67 | | | | | | | | | | | | | 1.04 | | |

EXAMPLE 11

The effect of the additive S of the invention on the incorporation of 40% of calcium carbonate in polypropylene was examined.

To ascertain the effect of the method of mixing on the properties of the final composition, two methods were used.

A first testing method was to dry blend calcium carbonate and a dispersant for 1 minute at 3600 rpm in a Henschel mixer in advance. In this method, the temperature was initially room temperature, but rose during the mixing operation. Calcium carbonate so surface treated with the dispersant was dry blended with polypropylene. The blend was molded at 230° C. by screw injection to prepare a test piece having a longitudinal size of 10 mm, a lateral size of 10 mm and a thickness of 1 mm.

A second testing method involved transferring the blend of the above three materials from the Henschel mixer to a high shear double concentric mixer, and mixed at 230° C. under high shear, and then injection molding the blend at 230° C. to prepare a test piece.

The results are shown in Table 17. The amount of the additive used is shown by % by weight based on polypropylene.

The results given in Table 17 show that polypropylene containing calcium carbonate treated with the additive of this invention has improved properties over the case of using the untreated material.

The addition of the additive of this invention in an amount of 1.0% brought about a marked improvement in impact strength. By using the double concentric screw, further improved properties were obtained. It is presumed that by the mixing under a high shear, the reactivity between the additive and the inorganic material was improved.

TABLE 17

| Run No. | Compounding recipe | Tensile strength (kg/cm$^2$) | Flexural stress (kg/mm$^2$) | Izod impact strength (notched) (kg-cm/cm) |
|---|---|---|---|---|
| 52(*) | No calcium carbonate | 350 | 1.7 | 3.8 |
| 53(*) | Calcium carbonate | 450 | 6.7 | 2.2 |
| 54 | Calcium carbonate + additive 0.5% | 390 | 4.7 | 3.0 |
| 55 | Calcium carbonate + additive 1.0% | 350 | 4.1 | 5.5 |
| 56 | Calcium carbonate(**) | 320 | 3.3 | 10.0 |

(*) Comparison
(**) According to method 2.

PRODUCTION EXAMPLE 10

One hundred grams of each of the polymers shown in Table 18 was dissolved in 500 ml of benzene, and the solution was put in a vessel equipped with a stirrer, an internal heating device, a vapor condenser and a liquid-solid feed inlet. With stirring, the solution was heated to 60° C. The reagent (1) and the reagent (2) were added in an amount of 0.1 mole each and reacted for about 1 hour. (As required, 0.15 mole of the reagent (3) was added.) Then, a small amount of methanol was added to stop the reaction. The reaction mixture was poured into 1 liter of methanol to coagulate the product. The product was dried by a vacuum dryer.

Thus, additives W and X were obtained.

TABLE 18

| Additive | W | X |
|---|---|---|
| Compound having and unsaturated bond | Polybutene (Mw = 3,750) | ethylene/propylene/diene copolymer (Mw = 100,000) |
| Reagent (1) | benzylidene stearylamine and acetyl chloride | N-hydroxymethyl benzamide |
| Reagent (2) | Tin tetrachloride | boron trifluoride etherate |

TABLE 18-continued

| Additive | W | X |
|---|---|---|
| Reagent (3) | — | toluenesulfonic acid |

PRODUCTION EXAMPLE 11

A 2-liter stainless steel polymerization reactor was washed, dried, and purged with dry nitrogen, and 150 g of 1,3-butadiene, 50 g of styrene, 890 g of benzene, 0.5 millimole of tetramethylethylenediamine and 1.8 millimoles of an n-hexane solution of n-butyl lithium were added. With stirring, the monomers were polymerized at 40° C. for 1 hour.

After the polymerization, 1.0 millimole of N-methylpyrrolidone was added and reacted with stirring for 10 minutes. Then, the contents in the reactor were poured into a 2.0% methanol solution of 2,6-di-t-butyl-p-cresol to coagulate the resulting polymer. The polymer was then dried at 60° C. and reduced pressure for 24 hours. The resulting polymer was designated as additive Y.

A polymer was produced under the same conditions as above except that N-methylpyrrolidone was not reacted. The resulting polymer was designated as additive Y'.

The additives Y and Y' had a bonded styrene content of 25%, and a weight average molecular weight of 150,000 as measured by GPC (calculated for polystyrenes).

PRODUCTION EXAMPLE 12

Ethylene/propylene/diene copolymer (Mw=100,000) (160 g) and 3 liters of benzene were put into a vessel equipped with a stirrer, an internal heating device, a vapor condenser and a liquid solid feed inlet. Benzylidene butylamine (20 millimoles) and 20 millimoles of acetyl chloride were added each as a benzene solution. Furthermore, 0.5 to 1 liter of methanol was added. The reaction mixture was cooled in a refrigerator. The resulting precipitate was washed with methanol, and dried to give an additive Z. The starting material was designated as additive Z'.

EXAMPLE 12

Additives O and W to Y and additive Y' (comparison) were each added to each of the following fuel oils in an amount of 300 ppm or 500 ppm. The low-temperature flowability and the detergent-dispersibility of the oils were evaluated. The results are shown in Table 19.

Fuel oil A: 20% boiling point 268° C., 90% boiling point 345° C., drying point 373° C.

Fuel oil B: 20% boiling point 221° C., 90% boiling point 332° C., drying point 359° C.

As measures of the low-temperature flowability of a petroleum intermediate distilled fuel oil, the pour point in accordance with JIS K-2204, and cold filter plugging filter (CFPP) in accordance with JIS K-2288 was measured. To determine detergent-dispersibility, an oxidation stability test of a lubricant was conducted in accordance with JIS K-2514, and by observing the state of adhesion of a lacquer to a varnish rod, the detergent dispersibility was evaluated.

The data given in Table 19 show that the additives to fuel oils in accordance with this invention have the function of a low temperature flowability improver and a dispersant.

TABLE 19

| Run No. | Fuel oil | Additive Type | Additive amount (ppm) | Flowability pour point (°C.) | Flowability CFPP (°C.) | Detergent-dispersibility Degree of lacquor adhesion |
|---|---|---|---|---|---|---|
| 57 | A | W | 500 | −13.5 | −11.0 | No adhering |
| 58 |   | X | 300 | −17.5 | −14.0 | matter |
| 59 |   | Y | 500 | −12.5 | −9.0 |   |
| 60(*) |   | — | — | −7.5 | −5.0 | No adhering |
| 61(*) |   | W' | 500 | −10.0 | −8.0 | matter |
| 62(*) |   | Y' | 500 | −9.5 | −7.0 |   |
| 63 | B | X | 500 | −22.5 | −17.0 | No adhering matter |
| 64 |   | P | 300 | −15.5 | −13.0 | adhesion thin |
| 65 |   | Y | 300 | −14.5 | −12.5 | adhesion thin |
| 66(*) |   | — | — | −9.0 | −6.5 | Adhesion thick |
| 67(*) |   | X' | 300 | −11.5 | −8.5 | Adhesion thick |
| 68(*) |   | Y' | 300 | −10.5 | −8 | Adhesion thick |

(*) indicates a comparison

EXAMPLE 13

Each of the additives Y, Y', Z, Z', G to J and G' to J' (G' to J' are the starting materials for the production of additives G to J) was added in an amount of 5 parts to 95 parts of a hydrogenated purified paraffinic mineral oil. The viscosity index of the resulting lubricant oil was measured in accordance with JIS K-2283. As a measure of shearing stability, the viscosity loss rate (calculated from the following equation) by ultrasonic radiation was measured in accordance with JPI-5S-29-88.

$$\text{Viscosity Loss rate (\%)} = \frac{V_o - V_f}{V_o} \times 10^6$$

$V_o$ is the dynamic viscosity before ultrasonic radiation (cst), and $V_f$ is the dynamic viscosity after the ultrasonic radiation (cst). The results are shown in Table 20.

The detergent dispersibility was evaluated by a test in accordance with JIS K-2514 for the degree of adhesion of a lacquer to a varnish rod. The results are shown in Table 21.

TABLE 20

| Run No. | Additive | Dynamic viscosity (cst) 40° C. | 100° C. | 100° C. (**) | V.I. | Low viscosity reduction rate (%) |
|---|---|---|---|---|---|---|
| 69(*) | — | 28.50 | 5.00 |   | 100 |   |
| 70 | Y | 45.44 | 9.31 | 193 | 9.18 | 1.40 |
| 71 | G | 39.01 | 6.28 | 5.71 | 139 | 9.08 |
| 72 | H | 36.54 | 6.66 | 6.01 | 140 | 9.76 |
| 73 | I | 37.54 | 6.98 | 6.72 | 145 | 3.72 |
| 74 | J | 40.01 | 7.55 | 7.28 | 159 | 3.68 |
| 75 | Z | 44.83 | 9.71 | 9.54 | 209 | 1.75 |

(*) comparison
(**) After the ultrasonication

TABLE 21

| Run No. | Detergent-dispersiblity Degree of lacquor adhesion |   |
|---|---|---|
| 76 | Y | No adhesion |
| 77 | G | Adhesion thin |
| 78 | H | No adhesion |
| 79 | I | Adhesion thin |
| 80 | J | No adhesion |
| 81 | Z | No adhesion |
| 82(*) | — | Adhesion thick |
| 83(*) | Y' | Adhesion thick |
| 84(*) | G' | Adhesion thick |
| 85(*) | H' | Adhesion thick |
| 86(*) | I' | Adhesion thick |
| 87(*) | J' | Adhesion thick |

TABLE 21-continued

| Run No. | Detergent-dispersiblity Degree of lacquor adhesion | |
|---------|---|---|
| 88(*) | Z' | Adhesion thick |

(*) Comparison

PRODUCTION EXAMPLE 13

Two hundred grams of A-B type styrene/butadiene block copolymer (styrene 67%; weight average molecular weight 120,000) was dissolved in 1.5 liters of dehydrated benzene. The solution was stirred in a closed glass vessel (separable flask) in a nitrogen atmosphere at 45° C., the compounds I, II and the Lewis acid indicated in Table 22 were added each as a benzene solution, and were reacted for 1 hour. Then, the reaction solution was poured into 3 liters of methanol to coagulate the polymer completely. The coagulum was separated as fine fragments, and washed. Then, the fine fragments of the coagulum were immersed in a 2% methanol solution of 2,6-di-t-butyl-p-cresol, washed, and then dried under reduced pressure at 60° C. for 24 hours to obtain a styrene/butadiene block copolymers (additives) (a), (b), (c) and (d) having an oxazine structure. The weight average molecular weights of these polymers were determined under the following conditions (calculated for standard polystyrene).

Column: GMH-6, two columns (made by Toso Co., Ltd.)
Temperature: 38° C.
Flow rate: 1.2 ml/min.
The presence of

TABLE 22

| Additive | Compound I | | Compound II | | Lewis acid | |
|---|---|---|---|---|---|---|
| | Type | Amount (mM) | Type | Amount (mM) | Type | Amount (mM) |
| (a) | benzylidene butylamine | 15.0 | acetyl chloride | 16.0 | SnCl$_4$ | 15.0 |
| (b) | benzylidene stearylamine | 18.8 | benzoyl chloride | 19.6 | TiCl$_4$ | 18.8 |
| (c) | benzylidene methylamine | 56.0 | acetyl chloride | 61.0 | SnCl$_4$ | 56.0 |
| (d) | — | — | — | — | — | — | bond was determined by the presence or absence of an ultraviolet absorption spectrum in 310–315 nm and a visible light absorption spectrum at 360 nm.

The same methods were used in the following examples.

TABLE 22

| Additive | Compound I | | Compound II | | Lewis acid | |
|---|---|---|---|---|---|---|
| | Type | Amount (mM) | Type | Amount (mM) | Type | Amount (mM) |
| (a) | benzylidene butylamine | 15.0 | acetyl chloride | 16.0 | SnCl$_4$ | 15.0 |
| (b) | benzylidene stearylamine | 18.8 | benzoyl chloride | 19.6 | TiCl$_4$ | 18.8 |
| (c) | benzylidene methylamine | 56.0 | acetyl chloride | 61.0 | SnCl$_4$ | 56.0 |
| (d) | — | — | — | — | — | — |

EXAMPLE 14

Production of an unsaturated polyester resin

Neopentylglycol 760 g and 410 g of isophthalic acid were reacted at 210° C. for 10 hours in a stream of an inert gas. Then, 620 g of propylene glycol and 1440 g of fumaric acid were added, and reacted at 200° C. for 15 hours to give an unsaturated polyester resin. The oxidation number of the resulting unsaturated polyester resin was 32.

Production of an unsaturated polyester resin composition

Thirty parts of additive (a), (b), (c) and (d), 70 parts by weight of the unsaturated polyester resin, 150 parts of styrene and 1 part of t-butyl perbenzoate were sufficiently mixed with stirring to prepare an unsaturated polyester resin composition.

Determination of phase separation

A portion of the unsaturated polyester resin was transferred to a beaker and allowed to stand at room temperature. The time which elapsed until the additive phase-separated onto the surface of the beaker was measured, and the results are shown in Table 23.

TABLE 23

| Run No. | | Additive | Time until phase separation occurred (hours) |
|---|---|---|---|
| Invention | 1 | (a) | 150 |
| | 2 | (b) | 135 |
| | 3 | (c) | 175 |
| Comparison | 4 | (d) | 15 |

By using the additives and the unsaturated polyester shown in Example 14, sheet molding compounds (SMC) were prepared in accordance with the compounding recipe shown in Table 24, and molded at 120° C. under a pressure of 100 kg/cm$^2$. Smooth molded articles without surface unevenness were obtained. The surface smoothness by visual observation and the linear shrinkages are shown in Table 25.

TABLE 24

| Compounding recipe | Amount (parts) |
|---|---|
| Unsaturated polyester resin (50% styrene solution) | 70 |
| Additive (30% styrene solution) | 30 |
| t-Butyl perbenzoate | 1 |
| Zinc stearate | 3 |
| Calcium carbonate | 150 |
| Magnesium oxide | 1 |

TABLE 24-continued

| Compounding recipe | Amount (parts) |
|---|---|
| Blue inorganic pigment | 8 |

TABLE 25

| Run No. | | Additive | Linear shrinkage (%) | Surface smoothness (*) |
|---|---|---|---|---|
| Invention | 5 | (a) | 0.06 | ⊚ |
| | 6 | (b) | 0.05 | ⊚ |
| | 7 | (c) | 0.08 | ∘ |
| Comparison | 8 | (d) | 0.5 | x |

(*) The evaluations were on the following scale.
⊚: excellent surface smoothness
∘: good surface smoothness
x: inferior surface smoothness

PRODUCTION EXAMPLE 14

Two hundred grams of styrene resin (the amount of styrene 97%; the amount of butadiene 3%; the weight average molecular weight 70,000) prepared by usual anionic polymerization was dissolved in 1.5 liters of dehydrated benzene, and while the solution was stirred in a closed glass vessel (separable flask) under an atmosphere of nitrogen, the compounds I, II and III indicated in Table 26 were added respectively as a benzene solution, and reacted for 1 hour. Then, the reaction solution was poured into 3 liters of methanol to coagulate the resin completely. The coagulum was separated as fine fragments, and washed. Then, the fine fragments of the coagulum were immersed in a 2% methanol solution of 2,6-di-t-butyl-p-cresol, washed, and then dried at 60° C. for 34 hours under reduced pressure to give styrene resins (e), (f) and (g) as additives.

EXAMPLE 15

In the same way as in Example 14, unsaturated polyester resin compositions were prepared and the times which elapsed until phase separation occurred were measured, and as in Example 14, molded products from the compositions were prepared, and their surface smoothnesses were determined by visual observation. The results are shown in Table 27.

TABLE 26

| Additive | Compound I | | Compound II | | Lewis acid | |
|---|---|---|---|---|---|---|
| | Type | Amount (mM) | Type | Amount (mM) | Type | Amount (mM) |
| (e) | benzylidene butylamine | 300 | benzoyl chloride | 360 | SnCl₄ | 300 |
| (f) | benzylidene aniline | 1000 | acetyl chloride | 1200 | TiCl₄ | 1000 |
| (g) | — | — | — | — | — | — |

TABLE 27

| Run No. | | Additive | Time until phase separation occurred (hours) | Surface smoothness* |
|---|---|---|---|---|
| Invention | 9 | (e) | 185 | ⊚ |
| | 10 | (f) | 155 | ⊚ |
| Comparison | 11 | (g) | 20 | x |

(*) The evaluations were on the following scale.
⊚: excellent surface smoothness
∘: good surface smoothness
x: inferior surface smoothness

PRODUCTION EXAMPLE 15

150 g of a partial hydrogenation product SEBS (the amount of styrene 34%; the iodine number 5; the weight average molecular weight 70,000, styrene-butadiene-styrene block copolymer) was dissolved in 1.5 liters of dehydrated benzene. While the solution was stirred at 45° C. in a closed glass vessel (separable flask) under an atmosphere of nitrogen, 150 mM of benzylidene stearylamine, 170 mM of acetyl chloride and 150 mM of SnCl₄ were added and reacted for 1 hour. Then, the reaction solution was poured into 3 liters of methanol to coagulate the resin completely. The coagulum was separated as fine fragments, and washed. The fine fragments of the coagulum was immersed in a 2% methanol solution of 2,6-di-t-butyl-p-cresol, washed, and then dried under reduced pressure at 60° C. for 24 hours to obtain a copolymer (h) as an additive.

EXAMPLE 16

As in Example 14, an unsaturated polyester resin composition was prepared. The time which elapsed until phase separation occurred in this composition was 150 hours. A molded article was prepared from the composition as in Example 14. The surface smoothness of the molded article was excellent.

PRODUCTION EXAMPLE 16

A 2-liter stainless steel polymerization reactor was washed and dried, and purged with dry nitrogen. Thereafter, 50 g of 1,3-butadiene, 100 g of styrene, 820 g of benzene, 0.5 mole of diethylene glycol dimethyl ether and 1.3 millimoles of n-butyllithium were added and the mixture was subjected to polymerization at 40° C. for 1 hour with stirring. After the completion of the polymerization reaction, 1.0 millimole of each of the modifiers indicated in Table 28 was added, and the mixture was stirred for 10 minutes. Then, the polymer solution in the reactor was transferred to a 2.0% methanol solution of 2,6-di-t-butyl-p-cresol to coagulate the polymer formed, and the polymer was dried at 60° C. for 24 hours under reduced pressure. Thus, styrene/butadiene copolymers (weight average molecular weight 90,000) (i) to (q) were obtained as additives.

EXAMPLE 17

Production of unsaturated polyester resin compositions

Unsaturated polyester resin compositions were prepared by mixing 30 parts of each of the additives obtained above, 70 parts of the unsaturated polyester resin produced in Example 14, 150 parts of styrene and 1 part of t-butyl perbenzoate with sufficient stirring.

Determination of phase separation

A portion of each of the above unsaturated polyester resin compositions was transferred to a beaker, and left to stand at room temperature. The time which elapsed until phase separation of the additive on the surface of the beaker occurred was measured. The results are shown in Table 28.

TABLE 28

| Run No. | | Additive | Modifier | Time until phase separation occurred (hours) |
|---|---|---|---|---|
| Invention | 12 | (i) | N-methylpyrrolidone | 155 |
| | 13 | (j) | N-phenylpyrrolidone | 120 |
| | 14 | (k) | N-methylpiperidone | 150 |
| | 15 | (l) | N-methyl-epislon-caprolactam | 145 |
| | 16 | (m) | 4,4'-bis(diethyl-amino)benzophenone | 130 |
| | 17 | (n) | 4-diethylaminobenzo-phenone | 120 |
| | 18 | (o) | 1,3-dimethylimid-azolidinone | 135 |
| | 19 | (p) | N-diethylaminobenz-aldehyde | 115 |
| Comparison | 20 | (q) | none | 15 |

By using the additives of (i) to (q) and the unsaturated polyester resin of Example 14, sheet molding compounds were prepared in accordance with the compounding recipe shown in Table 29, and molded at 150° C. under a pressure of 100 kg/cm² for 3 minutes. The resulting molded articles were smooth without surface unevenness. The surface smoothnesses of the molded articles determined by visual observation and the linear shrinkages of the molded articles are shown in Table 30.

TABLE 29

| Compounding recipe | Amount (parts) |
|---|---|
| Unsaturated polyester resin (50% styrene solution) | 70 |
| Additive (30% styrene solution) | 30 |
| t-Butyl perbenzoate | 1 |
| Zinc stearate | 3 |
| Calcium carbonate | 150 |
| Magnesium oxide | 1 |
| Blue inorganic pigment | 8 |

TABLE 30

| Run No. | | Additive | Linear shrinkage (%) | Surface smoothness* |
|---|---|---|---|---|
| Invention | 21 | (i) | 0.05 | ⊚ |
| | 22 | (j) | 0.06 | ⊚ |
| | 23 | (k) | 0.05 | ⊚ |
| | 24 | (l) | 0.08 | ⊚ |
| | 25 | (m) | 0.10 | ○ |
| | 26 | (n) | 0.04 | ⊚ |
| | 27 | (o) | 0.08 | ○ |
| | 28 | (p) | 0.08 | ○ |
| Comparison | 29 | (q) | 0.5 | x |

(*) The evaluations were on the following scale.
⊚: excellent surface smoothness
○: good surface smoothness
x: inferior surface smoothness

PRODUCTION EXAMPLE 17

A 2-liter stainless steel polymerization reactor was washed, dried and purged with dry nitrogen, and then 150 g of monomers indicated in Table 31, 820 g of benzene and n-butyllithium in the amount indicated in Table 10 were added. With stirring, the mixture was subjected to polymerization at 60° C. for 3 hours. After the completion of the polymerization, each of the modifiers shown in Table 10 was added in an equimolar amount with respect to the n-butyllithium. The reaction was carried out for 30 minutes with stirring. Then, 10 ml of methanol was added to stop the reaction. The polymer solution was transferred to a 2% methanol solution of 2,6-di-t-butyl-p-cresol to coagulate the resulting polymer. The coagulated polymer was dried under reduced pressure. Thus, additives (r) to (w) were obtained.

The microstructures and the weight average molecular weights of the additive polymers were measured, and the results are shown in Table 32.

TABLE 31

| Additive | Monomer (g) | | n-butyl lithium (mmol) | Modifier |
|---|---|---|---|---|
| | sytrene | butadiene | | |
| (r) | 0 | 150 | 30 | 4,4'-bis-(diethylamino)-benzophenone |
| (s) | 70 | 80 | 30 | 4,4'-bis-(diethylamino)-benzophenone |
| (t) | 0 | 150 | 30 | 4,4'-bis-(diethylamino)-benzophenone |
| (u) | 0 | 150 | 50 | N-methylpyrrolidone |
| (v) | 0 | 150 | 50 | none |
| (w) | 70 | 80 | 50 | none |

TABLE 32

| Additive | Polymer structure | | | | Weight average molecular weight (10³) |
|---|---|---|---|---|---|
| | Styrene content (%) | Microstructure of the butadiene portion (%)* | | | |
| | | cis | trans | vinyl | |
| (r) | 0 | 30 | 56 | 14 | 8 |
| (s) | 47 | 31 | 57 | 12 | 7 |
| (t) | 0 | 30 | 57 | 13 | 4 |
| (u) | 0 | 31 | 56 | 13 | 4 |
| (v) | 0 | 31 | 56 | 13 | 4 |
| (w) | 47 | 31 | 57 | 12 | 4 |

*Determined by the Hampton method.

EXAMPLE 18

Production of epoxy resin compositions

In accordance with the compounding recipe shown in Table 33, epoxy resin compositions were prepared using the additives (r) to (w) and the additives (x), (y) and (z) (acrylonitrile/butadiene copolymers).

TABLE 33

| Ingredient | Amount (parts) |
|---|---|
| Epoxy resin (bisphenol A-type epoxy resin having an epoxy equivalent of 185 to 195 eq/g) | 100 |
| Additive | 25 |
| Hexahydrophthalic anhydride | 80 |
| 2-Ethyl-4-methylimidazole | 1.8 |

Evaluation of cured articles

The resulting epoxy resin compositions were each cured by heating at 100° C. for 2 hours and then at 150° C. for 2 hours. The cured articles were each heat-treated at 50° C. for 24 hours and then immersed in water at 25° C. for 24 hours. Weight changes of the articles were measured, and percent water absorptions were determined.

Table 34 shows that the compositions in accordance with this invention have an improving effect in shrinkage and water absorption.

TABLE 34

| Run No. | | Additive | Volume shrinkage (%) | Water absorption (%) |
|---|---|---|---|---|
| Invention | 30 | (r) | 1.0 | 0.3 |
| | 31 | (s) | 1.0 | 0.3 |
| | 32 | (t) | 0.8 | 0.3 |
| | 33 | (u) | 0.6 | 0.3 |
| Comparison | 34 | (v) | 4.5 | 0.6 |
| | 35 | (w) | 4.0 | 0.6 |
| | 36 | (x)* | 2.5 | 0.4 |
| | 37 | (y)** | 2.5 | 0.5 |
| | 38 | (z)*** | 3.0 | 0.5 |

*Carboxyl-terminated butadiene/acrylonitrile copolymer (Hycar CTBN-1008USP; number average molecular weight 3500, a product of Ube Industries Co., Ltd.)
**Carboxyl-containing monomer/butadiene/acrylonitrile terpolymer (Nipol DN-601, number average molecular weight 3500, a product of Nippon Zeon Co., Ltd.)
***Butadiene/acrylonitrile copolymer (Nipol 1312, number average molecular weight 3500, a product of Nippon Zeon Co., Ltd.)

What is claimed is:

1. A stabilized fuel oil dispersion comprising a particulate substance dispersed in a fuel oil and a dispersion stabilizing effective amount of an additive comprising at least one oligomeric or polymeric compound having a $$>C=\overset{\oplus}{N}<$$

bond in the molecule, said additive having a weight average molecular weight of 100 to 300,000 and being compatible with the fuel oil.

2. The stabilized dispersion of claim 1 in which the dispersion stabilizing additive is an oligomeric or polymeric compound having an oxazolinium ion in the molecule.

3. The stabilized dispersion of claim 1 wherein the $>C=N^{\oplus}<$ bond is part of a heterocyclic ring and wherein the heterocyclic ring is present in the backbone chain of the oligomeric or polymeric compound.

4. The stabilized dispersion of claim 2 in which the oxazolinium ion is present at at least one end of the molecular chain.

5. The stabilized dispersion of claim 1 wherein the dispersion stabilizing additive comprises said at least one oligomeric or polymeric compound which is a reaction product of a living anion oligomer or polymer with at least one compound having a $$-\underset{\underset{X}{\|}}{C}-N<$$

bond in the molecule, wherein X is an oxygen atom, or sulfur atom, wherein said compound is selected from the group consisting of N-substituted amino ketones, N-substituted aminothioketones, N-substituted amino aldehydes, and N-substituted amino thioaldehydes.

6. The stabilized dispersion of claim 1 wherein the dispersion stabilizing additive is an oligomeric or polymeric compound selected from the group consisting of compounds of the following formula:

(1a) [structure with R1, R2, R3, R4, R5, O, N⊕=C, X⊖]

(1b) [structure]

(2a) [structure with S]

(2b) [structure with S]

(3a) [structure with O(or S)]

(3b) [structure with O(or S)]

(4a) [structure with N-R5]

(4b) [structure with N-R5]

(5a) [structure with CH-R5]

and (5b) [structure with CH-R5]

wherein $R_1$ represents a part of the backbone chain of the oligomeric or polymeric compound; $R_2$ represents a part of the backbone chain of the oligomeric or polymeric compound, or a hydrogen atom or a hydrocarbon group having not more than 6 carbon atoms; $R_3$, $R_4$ and $R_5$, which may be the same or different, each represent a hydrocarbon group at least part of which is substituted by a substituent selected from the group consisting of halogen atom, nitro group, epoxy group, carboxyl group and hydroxyether group; and $X^{\ominus}$ represents an anion.

7. The stabilized dispersion of claim 1 in which the particulate substance is in the form of a powder, flake or fiber having a particle size in the range of from 0.01 to 50 micrometers.

8. The stabilized dispersion of claim 1 wherein the dispersion stabilizing effective amount of the dispersion stabilizing additive is 0.01 to 20% by weight based on the weight of the oil.

9. The stabilized dispersion of claim 1 wherein the particulate substance is surface treated with at least 1% by weight of the dispersion stabilizing additive.

10. The stabilized dispersion of claim 1 wherein the dispersion stabilizing additive has a weight average molecular weight of from 1000 to 100,000.

11. The stabilized dispersion of claim 1 in which the particulate substance is at least one inorganic substance selected from the group consisting of inorganic reinforcing materials, metal compounds, inorganic fillers, inorganic pigments, carbon and sludges precipitated from heavy oils or lubricant oils.

12. The stabilized dispersion of claim 1 in which the particulate substance is at least one organic substance selected from the group consisting of low molecular weight organic compounds, waxes, lubricants, residues of distillation or petroleum, naphtha or asphalthene at atmospheric or reduced pressure, organic pigments and fine particles or chopped fibers of organic polymers.

13. The stabilized dispersion of claim 1 wherein the dispersion stabilizing additive comprises at least one oligomeric or polymeric compound which is a reaction product obtained by reacting an oligomeric or polymeric compound having a carbon-carbon double bond in the molecule, a compound having a —CH=N— bond in the molecule and an organic acid halide in the presence of a Lewis acid.

* * * * *